United States Patent
Ware et al.

(10) Patent No.: US 9,694,058 B2
(45) Date of Patent: Jul. 4, 2017

(54) LIGHT-MEDIATED ANTI-CELL PROLIFERATIVE COMPOSITIONS AND METHODS

(75) Inventors: Carl F Ware, Solana Beach, CA (US); Timothy C. Cheung, Wollstonecraft (AU); Theresia A. Banks, San Diego, CA (US)

(73) Assignee: LA JOLLA INSTITUTE FOR ALLERGY AND IMMUNOLOGY, La Jolla, CA (US)

( * ) Notice: Subject to any disclaimer, the term of this patent is extended or adjusted under 35 U.S.C. 154(b) by 1014 days.

(21) Appl. No.: 12/446,729

(22) PCT Filed: Oct. 25, 2007

(86) PCT No.: PCT/US2007/022711
§ 371 (c)(1),
(2), (4) Date: Feb. 8, 2010

(87) PCT Pub. No.: WO2008/051612
PCT Pub. Date: May 2, 2008

(65) Prior Publication Data
US 2010/0136061 A1    Jun. 3, 2010

Related U.S. Application Data

(60) Provisional application No. 60/854,420, filed on Oct. 25, 2006.

(51) Int. Cl.
| | |
|---|---|
| *A61K 39/00* | (2006.01) |
| *C12N 5/071* | (2010.01) |
| *C07K 14/52* | (2006.01) |
| *C07K 14/705* | (2006.01) |

(52) U.S. Cl.
CPC .... *A61K 39/0011* (2013.01); *C07K 14/70575* (2013.01); *C12N 5/067* (2013.01); *C12N 5/0672* (2013.01); *A61K 2039/5152* (2013.01); *A61K 2039/6006* (2013.01); *C12N 2501/105* (2013.01); *C12N 2501/11* (2013.01); *C12N 2501/33* (2013.01); *C12N 2503/02* (2013.01)

(58) Field of Classification Search
None
See application file for complete search history.

(56) References Cited

U.S. PATENT DOCUMENTS

| 6,590,090 B1 | 7/2003 | Nishi et al. ............... 536/23.5 |
| 2002/0064869 A1* | 5/2002 | Ebner et al. .............. 435/320.1 |
| 2003/0120042 A1* | 6/2003 | Yamada et al. ............ 530/350 |
| 2009/0092640 A1* | 4/2009 | Fu ........................... 424/277.1 |

OTHER PUBLICATIONS

Degli-Esposti et al. (J. Immunology 1997 158:1756-1762).*
Sedgmen et al. (Internatl. Immunol. Mar. 28, 2006, 18(5) 797-806).*
Musicki et al. (Internatl. Immunol. Feb. 25, 2010 22(5): 353-358).*
Cheung et al. (J. Immunol. 2010 185: 1949-1958).*
Rudikoff et al. (PNAS USA, 1982, 79: 1979-1983).*
Coleman et al. (Research in Immunology, 1994; 145(1): 33-36).*
Burgess et al. (J of Cell Bio. 111:2129-2138, 1990).*
Ibragimova and Wade (Biophysical Journal, Oct. 1999, vol. 77, pp. 2191-2198).*
Mauri, D.N., et al., LIGHT, a New Member of the TNF Superfaily, and Lymphotoxin α Are Ligands for Herpesvirus Entry Mediator, Immunity, 1998, 8:21-30.
Singh, N.P., et al., A Novel Approach to Cancer Immunotherapy: Tumor Cells Decorated with CD80 Generate Effective Antitumor Immunity, Cancer Research, 2003, 63:4067-4073.
Tamada, K., et al., Modulation of T-Cell-Mediated Immunity in Tumor and Graft-Versus-Host Disease Models Through the LIGHT Co-Stimulatory Pathway, Nature Medicine, 2000, 6:283-289.
Wang, J., et al., the Role of LIGHT in T Cell-Mediated Immunity, Immunologic Research, 2004, 30:201-214.
Zhai, Y., et al., LIGHT, A Novel Ligand for Lymphotoxin β Receptor and TR2/HVEM Induces Apoptosis and Suppresses In Vitro Tumor Formation Via Gene Transfer, J. Clin. Invest., 1988, 102:1142-1151.

* cited by examiner

*Primary Examiner* — Peter J Reddig
(74) *Attorney, Agent, or Firm* — Pillsbury Winthrop Shaw Pittman LLP

(57) ABSTRACT

The tumor-necrosis factor superfamily member LIGHT (p30; TNFSF-14) is a cytokine for inducing immune responses against tumors. A novel biochemical approach is used to decorate the surface of tumor cells with LIGHT. LIGHT decorated cells can be used to vaccinate and induce effective, sustained immunity against cells expressing neo or pathogen associated antigens. Variants of LIGHT are described that enhance binding to cellular receptors (e.g., LT beta receptor) and decrease regulation by inhibitors (e.g., Decoy Receptor 3) increasing ability to stimulate immunity.

9 Claims, 13 Drawing Sheets

LIGHT-MEDIATED ANTI-CELL PROLIFERATIVE COMPOSITIONS AND METHODS

RELATED APPLICATIONS

This application is the National Phase of International Application PCT/US2007/022711, filed Oct. 25, 2007, which designated the U.S. and that International Application was published under PCT Article 21(2) in English, and claims the benefit of priority to U.S. application Ser. No. 60/854,420, filed Oct. 25, 2006, which is expressly incorporated herein by reference in its entirety.

GOVERNMENT SPONSORSHIP

This invention was made with government support under Grant. R37AI03368 awarded by the National Institutes of Health, National Institute of Allergy and Infectious Diseases. The government has certain rights in the invention.

SEQUENCE LISTING

The instant application contains a Sequence Listing which has been submitted in ASCII format via EFS-Web and hereby incorporated by reference in its entirety. Said ASCII copy, created on Apr. 22, 2009, is named liai0379967.txt and is 20,951 bytes in size.

TECHNICAL FIELD

The invention relates to LTbeta receptor agonists (e.g., LIGHT, p30 polypeptide), and methods of treating undesirable or aberrant cell proliferation or hyperproliferative disorders, such as tumors, cancers, neoplasia and malignancies. The invention also relates to forms of LIGHT (p30 polypeptide) having altered affinity relative to native wild type LIGHT (p30 polypeptide), such as increased or greater affinity or avidity for LTbeta receptor or HVEM, or reduced or less binding affinity or avidity for Decoy Receptor 3 (DcR3).

INTRODUCTION

The tumor-necrosis factor superfamily member LIGHT (TNFSF-14) is a ligand for the Lymphotoxin-β receptor (LTβR), herpesvirus entry mediator (HVEM), and decoy receptor-3 (DcR3) (a molecule in humans expressed by human cancer cells). LIGHT in its membrane bound form also regulates the ability of HVEM to activate the inhibitory receptor BTLA (B and T lymphocyte attenuator) (Cheung, et al. Proc Natl Acad Sci USA 102:13218 (2005); Compaan, et al. J Biol Chem 280:39553 (2005); Gonzalez, et al. Proc Natl Acad Sci USA 102:1116 (2005); and Sedy, et al., Nat. Immunol. 6:90 (2005)). LIGHT has recently emerged as a cytokine for mediating anti-tumor responses.

LIGHT is a unique immunotherapeutic molecule through its ability to bind the LTβR, HVEM and DcR3. The LTβ Receptor regulates multiple genes that help organize lymphoid cells in tissues and in areas of inflammation (Ware, C. F. Annu Rev Immunol 23:787 (2005)). For instance, LTβR regulates expression of several chemokines, such as CCL21 (Cyster, J. G. Annu Rev Immunol. 23:127 (2005); and Dejardin, et al., Immunity 17:525 (2002)).

CCL21 and related chemokines are important for the trafficking of naïve T lymphocytes into lymphoid tissues during homeostasis, infections and perhaps into the tumor environment. The LTβR also serves as an important growth regulator for dendritic cells in lymphoid tissue that present antigen to T cells (Kabashima, et al., Immunity 22:439 (2005)). LIGHT interacts with HVEM on T cells providing a potent costimulating signal for T cell activation, expansion, and differentiation into tumor specific cytotoxic T cells (CTL). DcR3 can effectively compete with the binding of LIGHT to its signaling receptors, LTβR or HVEM. Recent studies report that membrane-bound LIGHT inhibits binding between HVEM and BTLA (Cheung, et al. Proc Natl Acad Sci USA 102:13218 (2005)). Thus, the triple-functionality of LIGHT makes it a unique molecule to enhance immunity.

SUMMARY

The invention provides cells having an LTbeta receptor agonist attached, conjugated or coupled to the membrane of a cell. In one embodiment, the LTbeta receptor agonist comprises LIGHT (p30 polypeptide), LTalpha1 beta2, LTalpha2 beta1, LTbeta or an LTbeta receptor antibody. In another embodiment, LTbeta receptor agonist comprises a chimeric protein a portion of which includes a binding portion, such as a ligand, receptor, antibody or antibody subsequence that binds to a cell membrane (e.g., a molecule present on the membrane).

Cells to which an LTbeta receptor agonist is attached, conjugated or coupled to the membrane include undesirable, abnormal or aberrant cells such as hyperproliferative cells (e.g., tumor cells, cancer cells, malignant cells, neoplastic cells and metastatic cells) and pathogen infected cells. Cells to which an LTbeta receptor agonist is attached, conjugated or coupled to the membrane include eukaryotic cells (e.g., mammalian, such as human), which can be dead or alive.

Cells to which an LTbeta receptor agonist is attached, conjugated or coupled to the membrane also include cells that express an antigen. In particular embodiments, a cell expresses an antigen from a tumor cell or a cancer cell antigen, a malignant cell, a neoplastic cell, or a metastatic cell antigen, a viral antigen, a bacterial antigen, a fungal antigen, or a parasite antigen.

In certain embodiments, LTbeta receptor agonist that is attached, conjugated or coupled to the membrane of a cell is not expressed from a nucleic acid in the cell that encodes the LTbeta receptor agonist. In other embodiments, where a LIGHT (p30 polypeptide) variant or polymorphic form is an LTbeta receptor agonist that is attached, conjugated or coupled to the membrane of a cell, the LIGHT (p30 polypeptide) variant or polymorphic form can be expressed from a nucleic acid in the cell that encodes the LIGHT (p30 polypeptide) variant or polymorphic form.

In additional embodiments, LTbeta receptor agonist is attached, conjugated or coupled to a molecule (e.g., a polypeptide such as an antibody, or a carbohydrate) present on the membrane of the cell. LTbeta receptor agonist attachment, conjugation or coupling to the membrane of the cell can be mediated by a covalent or non-covalent bond, e.g., via cross-linking. LTbeta receptor agonist attachment, conjugation or coupling to the membrane of the cell via covalent or non-covalent binding of LTbeta receptor agonist to an intermediary molecule, wherein the intermediary molecule is in turn covalently or non-covalently bound to a molecule present on the cell membrane. In certain aspects, an intermediary molecule includes a first moiety and a second moiety, for example, a first moiety is biotin or a biotin derivative, and a second moiety is avidin, neutravidin or streptavidin, or a derivative or amino acid variant thereof.

LTbeta receptor agonists include mammalian (e.g., human) forms. LTbeta receptor agonists can be full length native sequences such as full length sequence of LIGHT (p30 polypeptide), LTalpha1 beta2, LTalpha2 beta1, LTbeta or LTbeta receptor antibody, or subsequences thereof that retain at least partial LTbeta receptor agonist or binding activity. In particular embodiments, a subsequence includes an extracellular amino acid sequence of LIGHT (p30 polypeptide) (e.g., of LIGHT set forth in SEQ ID NO:1), a soluble form of LIGHT (p30 polypeptide) (e.g., of LIGHT set forth in SEQ ID NO:2), or LIGHT (p30 polypeptide) comprises LIGHTt66 (e.g., LIGHTt66 set forth as SEQ ID NO:2).

LTbeta receptor agonists include variant and polymorphic forms, such as variant and polymorphic forms of LIGHT (p30 polypeptide), LTalpha1 beta2, LTalpha2 beta1, LTbeta or LTbeta receptor antibody, or subsequences of variant and polymorphic forms thereof that retain at least partial LTbeta receptor agonist or binding activity. In particular embodiments, a LIGHT (p30 polypeptide) variant or polymorphic form has reduced or less affinity or avidity for DcR3 (Decoy receptor 3), as compared to native wild type LIGHT (p30 polypeptide) (e.g., SEQ ID NO:1), a LIGHT (p30 polypeptide) variant or polymorphic form has greater or increased affinity or avidity for LTβR or HVEM, as compared to native wild type LIGHT (p30 polypeptide) (e.g., SEQ ID NO:1); and a LIGHT (p30 polypeptide) variant or polymorphic form has greater or increased affinity or avidity for LTβR or HVEM as well as reduced or less affinity or avidity for DcR3 (Decoy receptor 3) as compared to native wild type LIGHT (p30 polypeptide). In more particular embodiments, a LIGHT (p30 polypeptide) variant or polymorphic form includes an amino acid sequence selected from any one of SEQ ID NOs:3 to 10.

The invention also provides methods of promoting, stimulating, inducing or increasing immunity against a hyperproliferative cell, tumor cell, cancer cell or metastatic cell, or pathogen infected cell. In one embodiment, a method includes administering to a subject an amount of a cell having LTbeta receptor agonist attached, conjugated or coupled to the cell membrane effective to promote, stimulate, induce or increase the subject's immunity against the hyperproliferative cell, tumor cell, cancer cell, metastatic cell or pathogen infected cell.

The invention also provides methods of treating a subject for undesirable or abnormal hyperproliferative cells, tumor cells, cancer cells, neoplastic cells, metastatic cells, or pathogen infected cells. In one embodiment, a method includes administering to the subject an amount of a cell having LTbeta receptor agonist attached, conjugated or coupled to the cell membrane effective to treat the subject for undesirable or abnormal hyperproliferative cells, tumor cells, cancer cells, neoplastic cells, metastatic cells, or pathogen infected cells.

Cells applicable in the methods include cells in which the LTbeta receptor agonist is LIGHT (p30 polypeptide), LIGHT (p30 polypeptide) chimera, LIGHT (p30 polypeptide) variant or polymorphic form, LTalpha1 beta2, LTalpha2 beta1, LTbeta and an LTbeta receptor antibody or antibody subsequence. Cells with LTbeta receptor agonist attached, conjugated or coupled to the membrane include those in which the LTbeta receptor agonist is not expressed from a nucleic acid in the cell. Cells in which a LIGHT (p30 polypeptide) variant or polymorphic form is attached, conjugated or coupled to the membrane of a cell, the LIGHT (p30 polypeptide) variant or polymorphic form can be expressed from a nucleic acid in the cell that encodes the LIGHT (p30 polypeptide) variant or polymorphic form. Cells include eukaryotic cells (e.g., mammalian, such as human), which can be dead or alive.

LTbeta receptor agonists applicable in the methods include LIGHT (p30 polypeptide), LIGHT (p30 polypeptide) chimera, LIGHT (p30 polypeptide) variant or polymorphic form, LTalpha1 beta2, LTalpha2 beta1, LTbeta and an LTbeta receptor antibody or antibody, full length and subsequences thereof, and variant and polymorphic forms thereof that retain at least partial LTbeta receptor agonist or binding activity (e.g., full length native LIGHT (p30 polypeptide), variant and polymorphic forms and subsequences thereof).

Target subjects appropriate for the methods include those in need of such treatment, such as a subject having or at risk of having undesirable or abnormal hyperproliferative cells, tumor cells, cancer cells, malignant cells, neoplastic cells or metastatic cells, or pathogen infected cells, that affect or involve any region, organ, tissue or biological system, such as hematopoeitic cells, brain, skin, nasopharynx, head, neck, lung, thyroid, kidney, liver, pancreas, stomach, intestine, colon, rectum, bladder, ovary, uterus, breast, prostate, bone, vagina, and penis.

Methods include reducing or decreasing metastasis, proliferation or numbers of hyperproliferative cells, tumor cells, cancer cells, neoplastic cells, metastatic cells, or pathogen infected cells, or inhibiting or preventing increased numbers or metastasis of the hyperproliferative cells, tumor cells, cancer cells, neoplastic cells, metastatic cells, or pathogen infected cells, or stabilizing numbers of the hyperproliferative cells, tumor cells, cancer cells, neoplastic cells, metastatic cells, or pathogen infected cells.

The invention further provides isolated and purified LIGHT (p30 polypeptide) amino acid sequences and subsequence thereof that have increased or greater affinity or avidity for LTbeta receptor or HVEM, or has reduced or less binding affinity or avidity for Decoy Receptor 3 (DcR3), relative to native wild type LIGHT (p30 polypeptide), such as LIGHT (p30 polypeptide) set forth in SEQ ID NO:1. In particular embodiments, a LIGHT (p30 polypeptide) amino acid sequence includes any one of SEQ ID NOs:3 to 10, or a subsequence thereof.

The invention moreover provides isolated and purified LIGHT (p30 polypeptide) nucleic acids that encode LIGHT (p30 polypeptide) amino acid sequences and subsequences thereof that have increased or greater affinity or avidity for LTbeta receptor or HVEM, or reduced or less binding affinity or avidity for Decoy Receptor 3 (DcR3), relative to native wild type LIGHT (p30 polypeptide), such as LIGHT (p30 polypeptide) set forth in SEQ ID NO:1. In particular embodiments, nucleic acids encode a sequence selected from any one of SEQ ID NOs:3 to 10, or a subsequence thereof.

The invention still further provides nucleic acids that hybridize or are complementary to a nucleic acid that encodes a LIGHT (p30 polypeptide) amino acid sequence selected from any one of SEQ ID NOs:3 to 10, or a subsequence thereof, but does not hybridize to a wild type native LIGHT (p30 polypeptide) sequence, such as SEQ ID NO:1.

The invention yet additionally provides vectors (e.g., expression vectors) that include and host cells (e.g., transformed cells) that express LIGHT (p30 polypeptide) amino acid sequence, such as variant and polymorphic forms. In particular embodiments, a nucleic acid encodes a LIGHT (p30 polypeptide) amino acid sequence selected from any one of SEQ ID NOs:3 to 10, or a subsequence thereof, and a transformed cell expresses a LIGHT (p30 polypeptide) amino acid sequence selected from any one of SEQ ID NOs:3 to 10.

DETAILED DESCRIPTION

Figure 1:
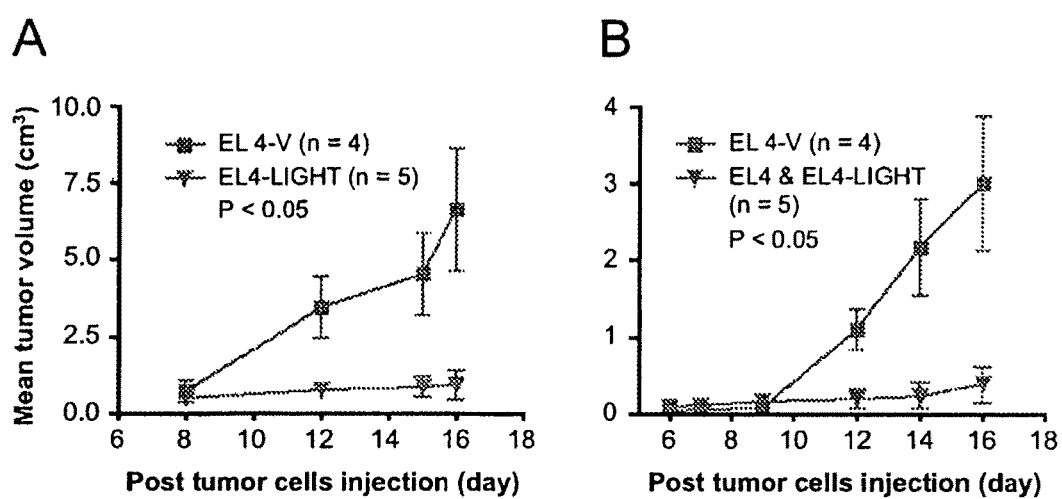
FIGS. 1A-1B. Suppression of tumor growth by human LIGHT. (A) EL4 cells transduced with empty retroviral vector (EL4-V), and EL4 transduced with retroviral vector encoding human LIGHT (EL4-LIGHT) were injected subcutaneously at $7.5 \times 10^5$ cells per C57Bl/6 (B6) mouse in groups of 4 or 5 mice per sample. The growth of EL4 and EL4-LIGHT tumors in syngeneic B6 mice was measured with a caliper over a period of 16 days after cell injections. EL4-injected mice quickly developed palpable tumors while the tumor development in the EL4-LIGHT injected group remained minimal or unmeasurable. (B) EL4-V cell were injected subcutaneously at $2.5 \times 10^5$ cells per mouse in both the control and the test groups. EL4-LIGHT cells ($2.5 \times 10^5$) were subsequently injected to each mouse of the test group. Tumor growth was measured as in (A). EL4-LIGHT cells strongly inhibited tumor growth of the parental EL4 cells.

The invention is based at least in part on cells that have been modified with an LTbeta receptor agonist. In particular, cells have LTbeta receptor agonist attached, conjugated or coupled to the membrane of a cell. Such cells are useful for treating undesirable or aberrant cell proliferation, hyperproliferation (e.g., hyperproliferative disorders), tumors, cancer, metastasis and neoplasia, as well as pathogen-infected cells.

In accordance with the invention, there are provided cells that have been modified with an LTbeta receptor agonist, including cells in which LTbeta receptor agonist has been attached, conjugated or coupled to the membrane of the cell. LTbeta receptor agonists include, for example, LIGHT (p30 polypeptide), LIGHT (p30 polypeptide) variants and polymorphic forms, LIGHT (p30 polypeptide) chimeras, LTalpha1 beta2, LTalpha2 beta1, LTbeta and an LTbeta receptor antibody. Cells modified with an LTbeta receptor agonist include undesirable cells or hyperproliferating cells, tumor cells, cancer cells, neoplastic cells, metastatic cells and pathogen infected cells. Cells modified with an LTbeta receptor agonist include eukaryotic cells, such as mammalian (e.g., primate or human) cells, which may be alive, non-viable or dead.

The invention is also based in part on LIGHT (p30 polypeptide) variants and polymorphic forms that exhibit altered affinity and/or avidity for a receptor. Such LIGHT (p30 polypeptide) variants and polymorphic forms have altered affinity and/or avidity for receptors, such as LTbeta receptor, HVEM, or DcR3 (Decoy receptor 3), as compared to native wild type LIGHT (p30 polypeptide), set forth as SEQ ID NO:1, for example.

In accordance with the invention, there are provided LIGHT (p30 polypeptide) variants that exhibit altered affinity and/or avidity for a receptor, such as LTbeta receptor, HVEM, or DcR3 (Decoy receptor 3). In one embodiment, a LIGHT (p30 polypeptide) variant exhibits reduced or less affinity and/or avidity for DcR3 (Decoy receptor 3) as compared to native wild type LIGHT (p30 polypeptide) set forth as SEQ ID NO:1. In another embodiment, a LIGHT (p30 polypeptide) variant exhibits increased or greater affinity and/or avidity for LTbeta receptor or HVEM as compared to native wild type LIGHT (p30 polypeptide) set forth as SEQ ID NO:1. LIGHT (p30 polypeptide) variants include polymorphic forms that have been isolated or purified from the naturally occurring environment, and have a sequence distinct from SEQ ID NO:1.

As used herein, the terms "attached, conjugated or coupled" to the membrane of the cell and grammatical variations thereof, when used in reference to an LTbeta receptor agonist, means that the agonist binds to or is physically attached to the membrane of a cell or a molecule (e.g., a polypeptide, carbohydrate, etc.) present on the membrane of a cell. Thus, for example, an LTbeta receptor agonist attached to or present on the membrane of a cell is not on the cell surface due to expression of an LTbeta receptor agonist from a nucleic acid in the cell that encodes the LTbeta receptor agonist. An LTbeta receptor agonist can be attached, conjugated or coupled to any molecule present on the membrane of the cell, such as a hyperproliferative cell, a tumor cell, cancer cell, neoplastic cell, metastatic cell, or a pathogen infected cell. LTbeta receptor agonist binding to the molecule on the cell membrane can be mediated by a covalent (e.g., cross-linking) or non-covalent (e.g., ligand-receptor, antibody-antigen) bond. Cells upon which LTbeta receptor agonist is bound can be or express an antigen selected from a tumor cell or a cancer cell antigen, a neoplastic cell or a metastatic cell antigen, a viral antigen, a bacterial antigen, a fungal antigen, or a parasite antigen.

LTbeta receptor agonists can be "attached, conjugated or coupled" to the membrane of the cell or an molecule present on the membrane of a cell by non-covalent or covalent bonds. Non-covalent bonds include hydrogen bonding, ionic interactions, Van der Waals interactions, and hydrophobic interactions. Non-limiting examples of non-covalent bonds are receptor-ligand, antibody-antigen and enzyme-substrate. Covalent bonds typically involve sharing of electrons and are also referred to as chemical bonds. Non-limiting examples of covalent bonds are amide bonds, non-natural and non-amide chemical bonds, other chemical bonds or coupling means including, for example, a carbon chain, such as carboxylic acids, multi-carbon chains (e.g., dicarboxylic acids, such as glutaric acid, succinic acid and adipic acid), glutaraldehyde, N-hydroxysuccinimide esters, bifunctional maleimides, N,N'-dicyclohexylcarbodiimide (DCC) or N,N'-diisopropylcarbodiimide (DIC). Groups alternative to amide bonds include, for example, ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in *Chemistry and Biochemistry of Amino Acids, Peptides and Proteins*, Vol. 7, pp 267-357, "Peptide and Backbone Modifications," Marcel Decker, N.Y.).

An LTbeta receptor agonist can be attached, conjugated or coupled to the membrane of the cell or an molecule present on the membrane of a cell via a distinct molecular entity, or an intermediary molecule. An intermediary molecule can be itself covalently or non-covalently bound to the membrane of the cell or an molecule present on the cell membrane. In one embodiment, an intermediary molecule includes two or more components such as a first moiety and a second moiety. In particular aspects, a first and second moiety binds to or physically interacts with each other, for example, a first moiety includes biotin or a biotin derivative, and a second moiety includes avidin, neutravidin or streptavidin, or a derivative or amino acid variant thereof. LTbeta receptor agonist binding to cell membrane or an molecule present on the membrane of a cell therefore includes binding to avidin, neutravidin or streptavidin, or a derivative or amino acid variant thereof that binds to an molecule present on the cell membrane. The LTbeta receptor agonist or the molecule to which the agonist is attached, conjugated or coupled, can each be bound via covalent or non-covalent binding to biotin or a biotin derivative, or avidin, neutravidin or streptavidin.

LTbeta receptor agonists include mammalian forms, such as primate and human LTbeta receptor agonists. Such agonists include "amino acid" "protein," "polypeptide" and "peptide" sequences. The terms "amino acid," "protein," "polypeptide" and "peptide" are used interchangeably herein to refer to two or more amino acids, or "residues," covalently linked by an amide bond or equivalent. Amino acid sequences can be linked by non-natural and non-amide chemical bonds including, for example, those formed with glutaraldehyde, N-hydroxysuccinimide esters, bifunctional maleimides, or N,N'-dicyclohexylcarbodiimide (DCC). Non-amide bonds include, for example, ketomethylene, aminomethylene, olefin, ether, thioether and the like (see, e.g., Spatola in *Chemistry and Biochemistry of Amino Acids, Peptides and Proteins*, Vol. 7, pp 267-357 (1983), "Peptide and Backbone Modifications," Marcel Decker, N.Y.).

LTbeta receptor agonists, chimeras and LIGHT (p30 polypeptide) include full length native wild type, variant and polymorphic forms of LTbeta receptor agonists, such as LIGHT (p30 polypeptide), HVEM and LIGHT (p30 polypeptide) chimeras that retain at least partial LTbeta receptor agonist or binding activity. Exemplary LTbeta receptor agonist variant and polymorphic forms include LIGHT (p30 polypeptide) with reduced or less affinity for DcR3 (Decoy receptor 3) as compared to native wild type LIGHT (p30 polypeptide), e.g., SEQ ID NO:1, LIGHT (p30 polypeptide) with increased or greater affinity or avidity for LTβR or HVEM as compared to native wild type LIGHT (p30 polypeptide), e.g., SEQ ID NO:1, as well as LIGHT (p30 polypeptide) with increased or greater affinity or avidity for LTβR or HVEM and with reduced or less affinity for DcR3 (Decoy receptor 3), as compared to native wild type LIGHT (p30 polypeptide), e.g., SEQ ID NO:1. Particular non-limiting variant and polymorphic forms of LIGHT (p30 polypeptide) include an amino acid sequence selected from any one of SEQ ID NOs:3 to 10.

Representative LIGHT (p30 polypeptide) sequences are as follows:

```
Full Length Human LIGHT (Amino Acid Sequence)
                                        (SEQ ID NO: 1)
MEESVVRPSVFVVDGQTDIPFTRLGRSHRRQSCSVAR

QLHWRLGEMVTRLPDGPAGSWEQLIQERRSHEVNPA

AHLTGANSSLTGSGGPLLWETQLGLAFLRGLSYHDGALVVTKAGYYYIYS

KVQLGGVGCPLGLASTITHGLYKRTPRYPEELELLVSQQSPCGRATSSSR

VWWDSSFLGGVVHLEAGEEVVVRVLDERLVRLRDGTRSYFGAFMV
```

The amino acid residues of the transmembrane domain are shaded. The amino acid residues of the extracellular domain of LIGHT are underlined.

```
Soluble Form of LIGHT (AKA: LIGHTt66, Amino Acid
Sequence)
                                        (SEQ ID NO: 2)
GEMVTRLPDGPAGSWEQLIQERRSHEVNPAAHLTGANSSLTGSGGPLLWE

TQLGLAFLRGLSYHDGALVVTKAGYYYIYSKVQLGGVGCPLGLASTITHG

LYKRTPRYPEELELLVSQQSPCGRATSSSRVWWDSSFLGGVVHLEAGEEV

VVRVLDERLVRLRDGTRSYFGAFMV

Human LIGHT E214K (Amino Acid Sequence)
                                        (SEQ ID NO: 3)
MEESVVRPSVFVVDGQTDIPFTRLGRSHRRQSCSVARVGLGLLLLLMGAG

LAVQGWFLLQLHWRLGEMVTRLPDGPAGSWEQLIQERRSHEVNPAAHLTG

ANSSLTGSGGPLLWETQLGLAFLRGLSYHDGALVVTKAGYYYIYSKVQLG

GVGCPLGLASTITHGLYKRTPRYPEELELLVSQQSPCGRATSSSRVWWDS

SFLGGVVHLEAGE VVVRVLDERLVRLRDGTRSYFGAFMV
```

The amino acid residue at position 214 of SEQ ID NO:3 is highlighted.

```
Human LIGHT S32L (Amino Acid Sequence)
                                        (SEQ ID NO: 4)
MEESVVRPSVFVVDGQTDIPFTRLGRSHRRQ CSVARVGLGLLLLLMGAG

LAVQGWFLLQLHWRLGEMVTRLPDGPAGSWEQLIQERRSHEVNPAAHLTG

ANSSLTGSGGPLLWETQLGLAFLRGLSYHDGALVVTKAGYYYIYSKVQLG

GVGCPLGLASTITHGLYKRTPRYPEELELLVSQQSPCGRATSSSRVWWDS

SFLGGVVHLEAGEEVVVRVLDERLVRLRDGTRSYFGAFMV
```

The amino acid residue at position 32 of SEQ ID NO:4 is highlighted.

```
Human LIGHT S9A (mutation from S to A at amino
acid position 9, amino acid sequence)
                                        (SEQ ID NO: 5)
MEESVVRP VFVVDGQTDIPFTRLGRSHRRQSCSVARVGLGLLLLLMGAG

LAVQGWFLLQLHWRLGEMVTRLPDGPAGSWEQLIQERRSHEVNPAAHLTG

ANSSLTGSGGPLLWETQLGLAFLRGLSYHDGALVVTKAGYYYIYSKVQLG
```

-continued

GVGCPLGLASTITHGLYKRTPRYPEELELLVSQQSPCGRATSSSRVWWDS

SFLGGVVHLEAGEEVVVRVLDERLVRLRDGTRSYFGAFMV

The amino acid residue at position 9 of SEQ ID NO:5 is highlighted.

Human LIGHT S27A (mutation from S to A at amino
acid position 27, amino acid sequence)
                                                (SEQ ID NO: 6)
MEESVVRPSVFVVDGQTDIPFTRLGR*HRRQSCSVARVGLGLLLLLMGAG

LAVQGWFLLQLHWRLGEMVTRLPDGPAGSWEQLIQERRSHEVNPAAHLTG

ANSSLTGSGGPLLWETQLGLAFLRGLSYHDGALVVTKAGYYYIYSKVQLG

GVGCPLGLASTITHGLYKRTPRYPEELELLVSQQSPCGRATSSSRVWWDS

SFLGGVVHLEAGEEVVVRVLDERLVRLRDGTRSYFGAFMV

The amino acid residue at position 9 of SEQ ID NO:6 is highlighted.

Human LIGHT S9A & S27A (mutation from S to A at
amino acid positions 9 and 27, amino acid
sequence)
                                                (SEQ ID NO: 7)
MEESVVRP*VFVVDGQTDIPFTRLGR*HRRQSCSVARVGLGLLLLLM

GAGLAVQGWFLLQLHWRLGEMVTRLPDGPAGSWEQLIQERRSHEVNPAAH

LTGANSSLTGSGGPLLWETQLGLAFLRGLSYHDGALVVTKAGYYIYSKV

QLGGVGCPLGLASTITHGLYKRTPRYPEELELLVSQQSPCGRATSSSRVW

WDSSFLGGVVHLEAGEEVVVRVLDERLVRLRDGTRSYFGAFMV

The amino acid residue at positions 9 and 27 of SEQ ID NO:7 are highlighted.

Human LIGHT S9A & S32L (mutation from S to A at
amino acid position 9 and S to L at position 32,
amino acid sequence)
                                                (SEQ ID NO: 8)
MEESVVRP*VFVVDGQTDIPFTRLGRSHRRQ*CSVARVGLGLLLLLM

GAGLAVQGWFLLQLHWRLGEMVTRLPDGPAGSWEQLIQERRSHEVNPAAH

LTGANSSLTGSGGPLLWETQLGLAFLRGLSYHDGALVVTKAGYYIYSKV

QLGGVGCPLGLASTITHGLYKRTPRYPEELELLVSQQSPCGRATSSSRVW

WDSSFLGGVVHLEAGEEVVVRVLDERLVRLRDGTRSYFGAFMV

The amino acid residue at positions 9 and 32 of SEQ ID NO:8 is highlighted.

Human LIGHT S27A & S32L (mutation from S to A at
amino acid position 27 and S to L at position 32,
amino acid sequence)
                                                (SEQ ID NO: 9)
MEESVVRPSVFVVDGQTDIPFTRLGR*HRRQ*CSVARVGLGLLLLLM

GAGLAVQGWFLLQLHWRLGEMVTRLPDGPAGSWEQLIQERRSHEVNPAAH

LTGANSSLTGSGGPLLWETQLGLAFLRGLSYHDGALVVTKAGYYIYSKV

QLGGVGCPLGLASTITHGLYKRTPRYPEELELLVSQQSPCGRATSSSRVW

WDSSFLGGVVHLEAGEEVVVRVLDERLVRLRDGTRSYFGAFMV

The amino acid residue at positions 27 and 32 of SEQ ID NO:9 are highlighted.

Human LIGHT S9A & S27A & S32L (mutation from S to
A at amino acid positions 9 and 27, and S to L at
position 32, amino acid sequence)
                                                (SEQ ID NO: 10)
MEESVVRP*VFVVDGQTDIPFTRLGR*HRRQ*CSVARVGLGLLLLLM

GAGLAVQGWFLLQLHWRLGEMVTRLPDGPAGSWEQLIQERRSHEVNPAAH

LTGANSSLTGSGGPLLWETQLGLAFLRGLSYHDGALVVTKAGYYYTYSKV

QLGGVGCPLGLASTITHGLYKRTPRYPEELELLVSQQSPCGPATSSSRVW

WDSSFLGGVVHLEAGEEVVVRVLDERLVRLRDGTRSYFGAFMV

The amino acid residue at positions 9, 27, and 32 of SEQ ID NO:10 are highlighted.

LTbeta receptor agonists also include subsequences of full length native wild type, variant and polymorphic forms of LTbeta receptor agonists, LIGHT (p30 polypeptide), HVEM and LIGHT (p30 polypeptide) chimeras. Exemplary lengths of LTbeta receptor agonists, chimeras and LIGHT (p30 polypeptide) include full length native wild type, variant and polymorphic forms of LTbeta receptor agonists, LIGHT (p30 polypeptide) chimeras, LIGHT (p30 polypeptide) and HVEM, as well as subsequences of LTbeta receptor agonists, LIGHT (p30 polypeptide) chimeras, LIGHT (p30 polypeptide) and HVEM that retain at least partial LTbeta receptor agonist or binding activity. Exemplary LTbeta receptor agonist subsequences include from about 5 to 15, 20 to 25, 25 to 50, 50 to 100, 100 to 150, 150 to 200, or 200 to 300 amino acid residues in length.

In particular embodiments, LTbeta receptor agonists, LIGHT (p30 polypeptide) chimeras and LIGHT (p30 polypeptide) and HVEM include or consist of an amino acid sequence of about 1 to 10, 10 to 20, 15 to 20, 20 to 30, 30 to 40, 40 to 50, 60 to 70, 70 to 80, 80 to 90, 90 to 100 or more residues. Specific non-limiting examples include soluble forms of LTbeta receptor agonist, for example, agonists that lack a transmembrane domain, e.g., an extracellular amino acid sequence of LIGHT (p30 polypeptide), set forth in any of SEQ ID NOs:1-10, or a soluble form of LIGHT (p30 polypeptide) set forth in SEQ ID NO:2 (LIGHTt66), that bind to and retain at least partial LTbeta receptor activity. Additional specific non-limiting examples include soluble forms of LIGHT (p30 polypeptide) variants and polymorphisms set forth in any of SEQ ID NOs:3-10, that bind to LTbeta receptor or HVEM, exhibit LTbeta receptor agonist activity, or exhibit reduced or less binding to DcR3, as compared to SEQ ID NO:1.

LTbeta receptor agonists, such as LIGHT (p30 polypeptide), LIGHT (p30 polypeptide) chimeras, LIGHT (p30 polypeptide) variants and polymorphic forms, and HVEM therefore include sequences with one or more (2, 3, 4, 5, etc.) conservative and non-conservative substitutions. A "conservative substitution" is a replacement of one amino acid by a biologically, chemically or structurally similar residue. Biologically similar means that the substitution is compatible with a biological activity, e.g., agonist activity. Structurally similar means that the amino acids have side chains with similar length, such as alanine, glycine and serine, or having similar size, or the structure of a first, second or additional domain is maintained. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, etc. Routine assays can be used to determine whether a variant or polymorphic form has activity, e.g., agonist activity or binding activity.

Specific examples include a substitution or deletion of one or more amino acid (e.g., 1-3, 3-5, 5-10, 10-20, or more) residues of an LTbeta receptor agonist, such as LIGHT (p30 polypeptide) variants and polymorphic forms. A variant or polymorphic sequence typically has 85%, 90%, 95%, 96%, 97%, 98%, or more identity to a reference sequence.

The term "identity" and "homology" and grammatical variations thereof mean that two or more referenced entities are the same. Thus, where two amino acid sequences are identical, they have the same amino acid sequence. "Areas, regions or domains of identity" mean that a portion of two or more referenced entities are the same. Thus, where two amino acid sequences are identical or homologous over one or more sequence regions, they share identity in these regions. Due to variation in the amount of sequence conservation between structurally and functionally related proteins, the amount of sequence identity required to retain a function or activity depends upon the protein, the region and the function or activity of that region. The term "complementary," when used in reference to a nucleic acid sequence means the reference regions are 100% complementary, i.e., exhibit 100% base pairing with no mismatches.

The extent of identity between two sequences can be ascertained using a computer program and mathematical algorithm known in the art. Such algorithms that calculate percent sequence identity (homology) generally account for sequence gaps and mismatches over the comparison region. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch-2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., *Proc. Natl. Acad. Sci. USA* 85:2444 (1988); Pearson, *Methods Mol. Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

LTbeta receptor agonists, such as LIGHT (p30 polypeptide), LIGHT (p30 polypeptide) chimeras, LIGHT (p30 polypeptide) variants and polymorphic forms, and HVEM sequences can be entirely composed of natural amino acids or synthetic, non-natural amino acids or amino acid analogues, or derivatized forms. Non-naturally occurring amino acid sequences include L-amino acid sequences, D-amino acid sequences and amino acid sequences with mixtures of L-amino acids and D-amino acids. In various embodiments, a LTbeta receptor agonist includes one or more D-amino acids substituted for L-amino acids, mixtures of D-amino acids and L-amino acids, or a sequence composed entirely of D-amino acid residues.

Amino acid sequences can be a linear or a cyclic structure, attached, conjugated or coupled to a distinct moiety (e.g., an intermediary), form intra or intermolecular disulfide bonds, be modified to include, for example, sugar or carbohydrate residues, phosphate groups, fatty acids, lipids, and also form higher order multimers or oligomers with the same or different amino acid sequence, e.g., different LTbeta receptor agonists, such as wild type and variants or polymorphisms of LIGHT (p30 polypeptide) in a multimer combination.

Additional examples of LTbeta receptor agonists include antibodies and antibody fragments. An "antibody" refers to any monoclonal or polyclonal immunoglobulin molecule, such as IgM, IgG, IgA, IgE, IgD, and any subclass thereof. Exemplary subclasses for IgG are $IgG_1$, $IgG_2$, $IgG_3$ and $IgG_4$. Specific examples of LTbeta receptor agonist antibodies include 3C8 and 4H8 (rat anti-mouse), goat polyclonal antibodies and mouse anti-human BDA8 antibody. Additional specific examples of LTbeta receptor agonist antibodies include fully human antibodies.

LTbeta receptor agonists include chimeric proteins in which a portion that is distinct from LTbeta receptor agonist. In other words, a chimeric LTbeta receptor agonist can include a portion that is distinct from a native wild type LTbeta receptor. Specific examples include an antigen, ligand, receptor or an antibody that binds to an antibody, receptor, ligand or antigen present on a cell membrane. Additional specific examples include protein A domains that bind immunoglobulin.

Peptides and peptidomimetics can be produced and isolated using methods known in the art. Peptides can be synthesized, whole or in part, using chemical methods known in the art (see, e.g., Caruthers (1980). *Nucleic Acids Res. Symp. Ser.* 215; Horn (1980); and Banga, A. K., *Therapeutic Peptides and Proteins, Formulation, Processing and Delivery Systems* (1995) Technomic Publishing Co., Lancaster, Pa.). Peptide synthesis can be performed using various solid-phase techniques (see, e.g., Roberge *Science* 269:202 (1995); Merrifield, *Methods Enzymol.* 289:3 (1997)) and automated synthesis may be achieved, e.g., using the ABI 431A Peptide Synthesizer (Perkin Elmer) in accordance with the manufacturer's instructions. Peptides and peptide mimetics can also be synthesized using combinatorial methodologies. Synthetic residues and polypeptides incorporating mimetics can be synthesized using a variety of procedures and methodologies known in the art (see, e.g., *Organic Syntheses* Collective Volumes, Gilman, et al. (Eds) John Wiley & Sons, Inc., NY). Modified peptides can be produced by chemical modification methods (see, for example, Belousov, *Nucleic Acids Res.* 25:3440 (1997); Frenkel, *Free Radic. Biol. Med.* 19:373 (1995); and Blommers, *Biochemistry* 33:7886 (1994).

The invention further provides nucleic acids encoding LIGHT (p30 polypeptide) variants and polymorphisms and subsequences thereof that are distinct from native naturally occurring LIGHT (p30 polypeptide) (e.g., SEQ ID NO:1). Nucleic acids also provided encode variants, polymorphic forms and subsequences of LIGHT (p30 polypeptide) that have reduced or exhibit no detectable binding to DcR3, as compared to native naturally occurring LIGHT (p30 polypeptide) (e.g., SEQ ID NO:1), but retain at least partial binding to one or more of LT beta receptor or HVEM. Nucleic acids further provided encode variants, polymorphic forms and subsequences of LIGHT (p30 polypeptide) that have increased or greater binding to one or more of LTbeta receptor and HVEM, as compared to native naturally occurring LIGHT (p30 polypeptide) (e.g., SEQ ID NO:1). In particular embodiments, a nucleic acid encodes any of SEQ ID NOs:3-10, or a subsequence thereof. In further embodiments, a nucleic acid is complementary to a nucleic acid sequence encoding any of SEQ ID NOs:3-10, or a subsequence thereof.

Nucleic acid, which can also be referred to herein as a gene, polynucleotide, nucleotide sequence, primer, oligonucleotide or probe refers to natural or modified purine- and pyrimidine-containing polymers of any length, either polyribonucleotides or polydeoxyribonucleotides or mixed polyribo-polydeoxyribo nucleotides and α-anomeric forms thereof. The two or more purine- and pyrimidine-containing polymers are typically linked by a phosphoester bond or analog thereof. The terms can be used interchangeably to refer to all forms of nucleic acid, including deoxyribonucleic acid (DNA) and ribonucleic acid (RNA). The nucleic acids can be single strand, double, or triplex, linear or circular. Nucleic acids include genomic DNA, cDNA, and antisense. RNA nucleic acid can be spliced or unspliced mRNA, rRNA, tRNA or antisense. Nucleic acids include naturally occurring, synthetic, as well as nucleotide analogues and derivatives.

As a result of the degeneracy of the genetic code, nucleic acids include sequences degenerate with respect to sequences encoding LIGHT (p30 polypeptide) variants and polymorphic forms of the invention. Thus, degenerate nucleic acid sequences encoding LIGHT (p30 polypeptide) variants and polymorphisms and subsequences thereof that are distinct from native naturally occurring LIGHT (p30 polypeptide), for example, SEQ ID NO:1, are provided.

Nucleic acid can be produced using any of a variety of known standard cloning and chemical synthesis methods, and can be altered intentionally by site-directed mutagenesis or other recombinant techniques known to one skilled in the art. Purity of polynucleotides can be determined through sequencing, gel electrophoresis, UV spectrometry.

Nucleic acids of the invention may be inserted into a nucleic acid construct in which expression of the nucleic acid is influenced or regulated by an "expression control element," referred to herein as an "expression cassette." The term "expression control element" refers to one or more nucleic acid sequence elements that regulate or influence expression of a nucleic acid sequence to which it is operatively linked. An expression control element can include, as appropriate, promoters, enhancers, transcription terminators, gene silencers, a start codon (e.g., ATG) in front of a protein-encoding gene, etc.

An expression control element operatively linked to a nucleic acid sequence controls transcription and, as appropriate, translation of the nucleic acid sequence. The term "operatively linked" refers to a juxtaposition wherein the referenced components are in a relationship permitting them to function in their intended manner. Typically expression control elements are juxtaposed at the 5' or the 3' ends of the genes but can also be intronic.

Expression control elements include elements that activate transcription constitutively, that are inducible (i.e., require an external signal for activation), or derepressible (i.e., require a signal to turn transcription off; when the signal is no longer present, transcription is activated or "derepressed"). Also included in the expression cassettes of the invention are control elements sufficient to render gene expression controllable for specific cell-types or tissues (i.e., tissue-specific control elements). Typically, such elements are located upstream or downstream (i.e., 5' and 3') of the coding sequence. Promoters are generally positioned 5' of the coding sequence. Promoters, produced by recombinant DNA or synthetic techniques, can be used to provide for transcription of the polynucleotides of the invention. A "promoter" is meant a minimal sequence element sufficient to direct transcription.

Nucleic acids may be inserted into a plasmid for propagation into a host cell and for subsequent genetic manipulation if desired. A plasmid is a nucleic acid that can be stably propagated in a host cell; plasmids may optionally contain expression control elements in order to drive expression of the nucleic acid. A vector is used herein synonymously with a plasmid and may also include an expression control element for expression in a host cell. Plasmids and vectors generally contain at least an origin of replication for propagation in a cell and a promoter. Plasmids and vectors are therefore useful for genetic manipulation of peptide and antibody encoding nucleic acids, producing peptides and antibodies or antisense, and expressing the peptides and antibodies in host cells or organisms, for example.

Bacterial system promoters include T7 and inducible promoters such as pL of bacteriophage λ, plac, ptrp, ptac (ptrp-lac hybrid promoter) and tetracycline responsive promoters. Insect cell system promoters include constitutive or inducible promoters (e.g., ecdysone). Mammalian cell constitutive promoters include SV40, RSV, bovine papilloma virus (BPV) and other virus promoters, or inducible promoters derived from the genome of mammalian cells (e.g., metallothionein IIA promoter; heat shock promoter) or from mammalian viruses (e.g., the adenovirus late promoter; the inducible mouse mammary tumor virus long terminal repeat). Alternatively, a retroviral genome can be genetically modified for introducing and directing expression of a protein or antibody in appropriate host cells.

Expression systems further include vectors designed for in vivo use. Particular non-limiting examples include adenoviral vectors (U.S. Pat. Nos. 5,700,470 and 5,731,172), adeno-associated vectors (U.S. Pat. No. 5,604,090), herpes simplex virus vectors (U.S. Pat. No. 5,501,979), retroviral vectors (U.S. Pat. Nos. 5,624,820, 5,693,508 and 5,674,703), BPV vectors (U.S. Pat. No. 5,719,054) and CMV vectors (U.S. Pat. No. 5,561,063).

Yeast vectors include constitutive and inducible promoters (see, e.g., Ausubel et al., In: *Current Protocols in Molecular Biology*, Vol. 2, Ch. 13, ed., Greene Publish. Assoc. & Wiley Interscience, 1988; Grant et al. *Methods in Enzymology*, 153:516 (1987), eds. Wu & Grossman; Bitter *Methods in Enzymology*, 152:673 (1987), eds. Berger & Kimmel, Acad. Press, N.Y.; and, Strathern et al., *The Molecular Biology of the Yeast Saccharomyces* (1982) eds. Cold Spring Harbor Press, Vols. I and II). A constitutive yeast promoter such as ADH or LEU2 or an inducible promoter such as GAL may be used (R. Rothstein In: *DNA Cloning, A Practical Approach*, Vol. 11, Ch. 3, ed. D. M. Glover, IRL Press, Wash., D.C., 1986). Vectors that facilitate integration of foreign nucleic acid sequences into a yeast chromosome, via homologous recombination for example, are known in the art. Yeast artificial chromosomes (YAC) are typically used when the inserted polynucleotides are too large for more conventional vectors (e.g., greater than about 12 Kb).

Expression vectors also can contain a selectable marker conferring resistance to a selective pressure or identifiable marker (e.g., beta-galactosidase), thereby allowing cells having the vector to be selected for, grown and expanded. Alternatively, a selectable marker can be on a second vector that is cotransfected into a host cell with a first vector containing an invention polynucleotide.

Selection systems include but are not limited to herpes simplex virus thymidine kinase gene (Wigler et al., *Cell* 11:223 (1977)), hypoxanthine-guanine phosphoribosyltransferase gene (Szybalska et al., *Proc. Natl. Acad. Sci. USA* 48:2026 (1962)), and adenine phosphoribosyltransferase (Lowy et al., *Cell* 22:817 (1980)) genes which can be employed in tk–, hgprt– or aprt– cells, respectively. Additionally, antimetabolite resistance can be used as the basis of selection for dhfr, which confers resistance to methotrexate (O'Hare et al., *Proc. Natl. Acad. Sci. USA* 78:1527 (1981)); the gpt gene, which confers resistance to mycophenolic acid (Mulligan et al., *Proc. Natl. Acad. Sci. USA* 78:2072 (1981)); neomycin gene, which confers resistance to aminoglycoside G-418 (Colberre-Garapin et al., *J. Mol. Biol.* 150:1 (1981)); puromycin; and hygromycin gene, which confers resistance to hygromycin (Santerre et al., *Gene* 30:147 (1984))). Additional selectable genes include trpB, which allows cells to utilize indole in place of tryptophan; hisD, which allows cells to utilize histinol in place of histidine (Hartman et al., *Proc. Natl. Acad. Sci. USA* 85:8047 (1988)); and ODC (ornithine decarboxylase), which confers resistance to the ornithine decarboxylase inhibitor, 2-(difluoromethyl)-DL-ornithine, DFMO (McConlogue (1987) In: *Current Communications in Molecular Biology*, Cold Spring Harbor Laboratory).

Host cells that express a LIGHT (p30 polypeptide) variant or polymorphic amino acid sequence are also provided. Such cells which have a nucleic acid encoding LIGHT (p30 polypeptide) variant or polymorphic amino acid sequence introduced into the cell are referred to as a transformed cell. Host and transformed cells include cells that do not express LIGHT (p30 polypeptide) variant or polymorphic amino acid sequence, but are used to propagate nucleic acid or vector which includes a nucleic acid encoding a LIGHT (p30 polypeptide) variant or polymorphic amino acid sequence, or subsequence thereof. Exemplary host and transformed cells express an amino acid sequence selected from any one of SEQ ID NOs:3 to 10. In one embodiment, a host or transformed cell is a prokaryotic cell. In another embodiment, a host or transformed cell is a eukaryotic cell. In various aspects, the eukaryotic cell is a yeast or mammalian (e.g., primate, human, etc.) cell.

Host and transformed cells include but are not limited to microorganisms such as bacteria and yeast; and plant, insect and mammalian cells. For example, bacteria transformed with recombinant bacteriophage nucleic acid, plasmid nucleic acid or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); and animal cell systems infected with recombinant virus expression vectors (e.g., retroviruses, adenovirus, vaccinia virus), or transformed animal cell systems engineered for transient or stable propagation or expression, are provided.

Cells in which an LTbeta receptor agonist has been attached, conjugated or coupled to the membrane of the cell or to an molecule present on the cell, such as LIGHT (p30 polypeptide), LIGHT (p30 polypeptide) chimeras, LTalpha1 beta2, LTalpha2 beta1, LTbeta or an LTbeta receptor antibody, LIGHT (p30 polypeptide) variants and polymorphisms and subsequences thereof, as well as nucleic acids encoding LIGHT (p30 polypeptide) variants and polymorphisms and subsequences thereof include isolated or purified forms. The term "isolated," when used as a modifier of a composition, means that the composition is made by the hand of man or is separated, substantially completely or at least in part, from the naturally occurring in vivo environment. Generally, an isolated composition is substantially free of one or more materials with which it normally associates with in nature, for example, one or more protein, nucleic acid, lipid, carbohydrate, cell membrane. The term "isolated" does not exclude alternative physical forms of the composition, such as multimers/oligomers, variants, modifications or derivatized forms, or forms expressed in host cells produced by the hand of man. The term "isolated" also does not exclude forms (e.g., pharmaceutical formulations and combination compositions) in which there are combinations therein, any one of which is produced by the hand of man.

An "isolated" composition can also be "purified" when free of some, a substantial number of, most or all of the materials with which it typically associates with in nature. Thus, a LIGHT (p30 polypeptide) variant or polymorphism that also is substantially pure does not include polypeptides or polynucleotides present among millions of other sequences, such as proteins of a protein library or nucleic acids in a genomic or cDNA library, for example. A "purified" composition can be combined with one or more other molecules.

In accordance with the invention, there are provided mixtures or combination compositions. In one embodiment, a mixture includes two or more cells in which an LTbeta receptor agonist has been attached, conjugated or coupled, each of which cells optionally have a different LTbeta receptor agonist attached thereto. In another embodiment, a mixture includes two or more LIGHT (p30 polypeptide) sequences, such as a variant or polymorphism and a wild type LIGHT (p30 polypeptide), or a first LIGHT (p30 polypeptide) variant or polymorphism and a second LIGHT (p30 polypeptide) variant or polymorphism different from the first LIGHT (p30 polypeptide) variant or polymorphism. In a further embodiment, a mixture includes a pharmaceutically acceptable carrier or excipient, i.e., a pharmaceutical composition or pharmaceutical formulation.

Compositions such as cells modified with an LTbeta receptor agonist and LIGHT (p30 polypeptide) variants and polymorphic amino acid sequences can be used to target undesirable, aberrant or abnormal cells, hyperproliferative cells such as tumor, cancer, neoplastic and metastatic cells, and pathogen infected cells for lysis, cell death or apoptosis. Disorders treatable in accordance with the invention therefore include undesirable, aberrant or abnormal cell proliferation and hyperproliferative cells and disorders, for example, a subject having or at risk of undesirable, aberrant cell or abnormal hyperproliferative cells, tumor cells, cancer cells, neoplastic cells, metastatic cells, or pathogen infected cells.

Cells modified with an LTbeta receptor agonist include cells that express one or more antigens of the target undesirable, aberrant or abnormal cells or hyperproliferating cells, tumor cells, cancer cells, neoplastic cells, metastatic cells and pathogen infected cells are applicable in various methods. Thus, to target undesirable, aberrant or abnormal cells, hyperproliferative cells, tumor, cancer, neoplastic and metastatic cells, these cells can be modified to have an LTbeta receptor agonist attached, conjugated or coupled to the cell membrane, and the modified cells are then in turn used to target the undesirable, aberrant or abnormal cells, hyperproliferative cells, tumor, cancer, neoplastic, metastatic or pathogen infected cells for lysis, cell death or apoptosis. In this way, cells so modified can be used to target the undesirable, aberrant or abnormal cells, hyperproliferative cells, tumor, cancer, neoplastic and metastatic cells, and pathogen infected cells.

In accordance with the invention, there are provided methods of promoting, stimulating, inducing or increasing immunity against a hyperproliferative cell, tumor cell, cancer cell, neoplastic cell or metastatic cell, or pathogen infected cell. In one embodiment, a method includes administering to a subject or contacting a subject with an amount of a cell having LTbeta receptor agonist attached, conjugated or coupled to the cell membrane sufficient to promote, stimulate, induce or increase the subject's immunity against the hyperproliferative cell, tumor cell, cancer cell, neoplastic cell metastatic cell or pathogen infected cell.

In accordance with the invention, there are also provided methods of treating a subject for undesirable or abnormal hyperproliferative cells, tumor cells, cancer cells, neoplastic cells, metastatic cells, or pathogen infected cells. In one embodiment, a method includes administering to the subject or contacting a subject with an amount of a cell having LTbeta receptor agonist attached, conjugated or coupled to the cell membrane effective to treat the subject for undesirable or abnormal hyperproliferative cells, tumor cells, cancer cells, neoplastic cells, metastatic cells, or pathogen infected cells.

In various aspects, the LTbeta receptor agonist includes LIGHT (p30 polypeptide), LTalpha1 beta2, LTalpha2 beta1, LTbeta or an LTbeta receptor antibody. In a particular aspect, an LTbeta receptor agonist includes LIGHT (p30 polypeptide) variant or polymorphic sequence, e.g., LIGHT (p30 polypeptide) with increased or greater binding affinity for LTbeta receptor or HVEM, or reduced or less binding affinity or avidity for DcR3, such as any of SEQ ID NOs:1, 2-10 alone, or in combination. In an additional particular aspect, an antibody is an agonist that stimulates or increases activity of LTbeta receptor.

The term "hyperproliferative disorder" refers to any undesirable, aberrant or abnormal cell survival (e.g., failure to undergo programmed cell death or apoptosis), growth or proliferation. Such disorders include benign hyperplasias, non-metastatic tumors and metastatic (neoplastic) tumors and cancers. Undesirable, aberrant or abnormal cell proliferation and hyperproliferative disorders can affect any cell, tissue, organ, region or system in a subject. A tumor can arise from a multitude of tissues and organs, including but not limited to breast, lung, nasopharynx, thyroid, head and neck, brain, lymphoid, gastrointestinal (mouth, esophagus, stomach, small intestine, colon, rectum), genito-urinary tract (uterus, ovary, cervix, bladder, vagina, testicle, penis, prostate), kidney, pancreas, liver, bone, muscle, skin, which may or may not metastasize to other secondary sites. Undesirable or aberrant cell proliferation and hyperproliferative disorders can affect any cell or tissue type, e.g., carcinoma, sarcoma, melanoma, neural, and reticuloendothelial or hematopoietic neoplastic cells and disorders (e.g., myeloma, lymphoma or leukemia). Undesirable or aberrant cell proliferation and hyperproliferative disorders can be present in a subject locally, regionally or systemically.

The terms "tumor," "cancer" and "neoplasia" are used interchangeably and refer to a cell or population of cells whose growth, proliferation or survival is greater than growth, proliferation or survival of a normal counterpart cell, e.g. a cell proliferative or differentiative disorder. Typically, the growth is uncontrolled. The term "malignancy" refers to invasion of nearby tissue. The term "metastasis" refers to spread or dissemination of a tumor, cancer or neoplasia to more distal tissues or sites within the subject.

The term "pathogen infected cell" refers to cells such as a autologous human blood cell infected with a virus, or is induced (transformed) to express a viral, bacterial or parasite (pathogen) gene or genes that may stimulate immunity when that cell also has attached, conjugated or coupled thereto an LTbeta receptor agonist. Administering such pathogen infected cells that have attached, conjugated or coupled thereto an LTbeta receptor agonist allows the expressed pathogen antigens to induce an immune response (e.g., protective immunity) against the antigen.

The term "contacting" means direct or indirect binding or interaction between two or more entities (e.g., between LTbeta receptor and an agonist, a cell in which LTbeta receptor agonist has been attached, conjugated or coupled to the membrane and a subject, etc.). Contacting as used herein includes in solution, in solid phase, in vitro, ex vivo, in a cell and in vivo. Contacting in vivo can be referred to as administering, or administration.

Cells comprising a tumor may be aggregated in a cell mass or be dispersed. A "solid tumor" refers to neoplasia or metastasis that typically aggregates together and forms a mass. Specific non-limiting examples include visceral tumors such as melanomas, breast, pancreatic, uterine and ovarian cancers, testicular cancer, including seminomas, gastric or colon cancer, hepatomas, adrenal, renal and bladder carcinomas, lung, head and neck cancers and brain tumors/cancers.

Carcinomas, which refer to malignancies of epithelial or endocrine tissue, include respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from the uterus, cervix, lung, prostate, breast, head and neck, colon, pancreas, testes, adrenal, kidney, esophagus, stomach, liver and ovary. The term also includes carcinosarcomas, e.g., which include malignant tumors composed of carcinomatous and sarcomatous tissues. Adenocarcinoma includes a carcinoma of a glandular tissue, or in which the tumor forms a gland like structure.

Sarcomas refer to malignant tumors of mesenchymal cell origin. Exemplary sarcomas include for example, lymphosarcoma, liposarcoma, osteosarcoma, chondrosarcoma, leiomyosarcoma, rhabdomyosarcoma and fibrosarcoma.

Neural neoplasias include glioma, glioblastoma, meningioma, neuroblastoma, retinoblastoma, astrocytoma, oligodendrocytoma.

A "liquid tumor," which refers to neoplasia that is diffuse in nature, as they do not typically form a solid mass. Particular examples include neoplasia of the reticuloendothelial or hematopoetic system, such as lymphomas, myelomas and leukemias. Non-limiting examples of leukemias include acute and chronic lymphoblastic, myeolblastic and multiple myeloma. Typically, such diseases arise from poorly differentiated acute leukemias, e.g., erythroblastic leukemia and acute megakaryoblastic leukemia. Specific myeloid disorders include, but are not limited to, acute promyeloid leukemia (APML), acute myelogenous leukemia (AML) and chronic myelogenous leukemia (CML). Lymphoid malignancies include, but are not limited to, acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Specific malignant lymphomas include, non-Hodgkin lymphoma and variants, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

The tumor, cancer, malignancy or neoplasia, may be in any stage, e.g., early or advanced, such as a stage I, II, III, IV or V tumor. The tumor may have been subject to a prior treatment or be stabilized (non-progressing) or in remission.

Cells in which LTbeta receptor agonist has been attached, conjugated or coupled to the membrane, LIGHT (p30 polypeptide) variants and polymorphic forms, and methods of the invention include anti-proliferative, anti-tumor, anti-cancer, anti-neoplastic treatments, protocols and therapies, which include any other composition, treatment, protocol or therapeutic regimen that inhibits, decreases, retards, slows, reduces or prevents a hyperproliferative disorder, such as tumor, cancer, malignant or neoplastic growth, progression, metastasis, proliferation or survival, or worsening in vitro or in vivo. Particular non-limiting examples of an anti-proliferative (e.g., tumor or cancer) therapy include chemotherapy, immunotherapy, radiotherapy (ionizing or chemical), local thermal (hyperthermia) therapy and surgical resection. Any composition, treatment, protocol, therapy or regimen having an anti-cell proliferative activity or effect can be used in combination with a cell in which LTbeta receptor agonist has been attached, LIGHT (p30 polypeptide) variants and polymorphic forms, in a method of the invention.

Anti-proliferative or anti-tumor compositions, therapies, protocols or treatments include those that prevent, disrupt, interrupt, inhibit or delay cell cycle progression or cell proliferation; stimulate or enhance apoptosis or cell death, inhibit nucleic acid or protein synthesis or metabolism, inhibit cell division, or decrease, reduce or inhibit cell survival, or production or utilization of a necessary cell survival factor, growth factor or signaling pathway (extracellular or intracellular). Non-limiting examples of chemical agent classes having anti-cell proliferative and anti-tumor activities include alkylating agents, anti-metabolites, plant extracts, plant alkaloids, nitrosoureas, hormones, nucleoside and nucleotide analogues. Specific examples of drugs having anti-cell proliferative and anti-tumor activities include cyclophosphamide, azathioprine, cyclosporin A, prednisolone, melphalan, chlorambucil, mechlorethamine, busulphan, methotrexate, 6-mercaptopurine, thioguanine, 5-fluorouracil, cytosine arabinoside, AZT, 5-azacytidine (5-AZC) and 5-azacytidine related compounds such as decitabine (5-aza-2' deoxycytidine), cytarabine, 1-beta-D-arabinofuranosyl-5-azacytosine and dihydro-5-azacytidine, bleomycin, actinomycin D, mithramycin, mitomycin C, carmustine, lomustine, semustine, streptozotocin, hydroxyurea, cisplatin, mitotane, procarbazine, dacarbazine, taxol, vinblastine, vincristine, doxorubicin and dibromomannitol.

Additional agents that are applicable with the compositions and methods can be employed. For example, monoclonal antibodies that bind tumor cells or oncogene products, such as Rituxan® and Herceptin (Trastuzumab)(anti-Her-2 neu antibody), Bevacizumab (Avastin), Zevalin, Bexxar, Oncolym, 17-1A(Edrecolomab), 3F8 (anti-neuroblastoma antibody), MDX-CTLA4, Campath®, Mylotarg, IMC-C225 (Cetuximab), aurinstatin conjugates of cBR96 and cAC10 (Doronina et al. *Nat. Biotechnol.* 21:778 (2003)) can be used in combination with, inter alia, a modified cell or LIGHT (p30 polypeptide) variant or polymorphic form in accordance with the invention.

Methods of treating a tumor, cancer, neoplasia malignancy, or pathogen infected cells, methods of treating a subject in need of due to having or at risk of having a tumor, cancer, neoplasia, malignancy, or pathogen infected cells and methods of increasing effectiveness or improving an anti-tumor, anti-cancer, anti-neoplasia, anti-malignancy, or anti-pathogen infected cell therapy are provided. In respective embodiments, a method includes administering to a subject with or at risk of a tumor, cancer, neoplasia, malignancy, or pathogen infected cells an amount of cell in which LTbeta receptor agonist has been attached, conjugated or coupled to the membrane of the cell, or an amount of a variant and polymorphic form of LIGHT (p30 polypeptide), sufficient to treat the tumor, cancer, neoplasia, malignancy or pathogen infected cells; administering to the subject an amount of a cell in which LTbeta receptor agonist has been attached, conjugated or coupled to the membrane of the cell, or a LIGHT (p30 polypeptide) variant or polymorphic form, sufficient to treat the subject; and administering to a subject that is undergoing or has undergone tumor, cancer, neoplasia, malignancy therapy or therapy for pathogen infected cells, an amount of a cell in which LTbeta receptor agonist has been attached, conjugated or coupled to the membrane of the cell, or variant or polymorphic form of LIGHT (p30 polypeptide), sufficient to increase effectiveness of the anti-tumor, anti-cancer, anti-neoplasia, anti-malignancy or anti-pathogen infected cell therapy.

Methods of the invention may be practiced prior to (i.e. prophylaxis), concurrently with or after evidence of the presence of undesirable, aberrant or abnormal cell proliferation or a hyperproliferative disorder, or pathogen infected cells e.g., one or more symptoms. Administering cells in which LTbeta receptor agonist has been attached, conjugated or coupled to the membrane, or a LIGHT (p30 polypeptide) variant or polymorphic form, prior to, concurrently with or immediately following development of a symptom of undesirable, aberrant or abnormal cell proliferation, a hyperproliferative disorder or pathogen infected cells may decrease the occurrence, frequency, severity, progression, or duration of one or more symptoms in the subject. In addition, administering cells in which LTbeta receptor agonist has been attached, conjugated or coupled to the membrane, or a LIGHT (p30 polypeptide) variant or polymorphic form, prior to, concurrently with or immediately following development of one or more symptoms may decrease or prevent the spread of hyperproliferating cells (e.g., tumor or cancer metastasis) or pathogen infected cells to other regions, tissues or organs in a subject.

Cells having LTbeta receptor attached, conjugated or coupled to the membrane, LIGHT (p30 polypeptide) variants and polymorphic forms, and the methods of the invention, such as treatment methods, can provide a detectable or measurable therapeutic benefit or improvement to a subject. A therapeutic benefit or improvement is any measurable or detectable, objective or subjective, transient, temporary, or longer-term benefit to the subject or improvement in the condition, disorder or disease, an adverse symptom, consequence or underlying cause, of any degree, in a tissue, organ, cell or cell population of the subject. Therapeutic benefits and improvements include, but are not limited to, reducing or decreasing occurrence, frequency, severity, progression, or duration of one or more symptoms or complications associated with a disorder, disease or condition, or an underlying cause or consequential effect of the disorder, disease or condition. Cells having LTbeta receptor attached, conjugated or coupled to the membrane, LIGHT (p30 polypeptide) variants and polymorphic forms, and methods of the invention therefore include providing a therapeutic benefit or improvement to a subject.

In a method of the invention in which a therapeutic benefit or improvement is a desired outcome, cells in which LTbeta receptor agonist has been attached, conjugated or coupled to the membrane, or LIGHT (p30 polypeptide) variants and polymorphic forms, can be administered in a sufficient or effective amount to a subject in need thereof. An "amount sufficient" or "amount effective" refers to an amount that provides, in single or multiple doses, alone or in combination, with one or more other compositions (therapeutic agents such as a chemotherapeutic or immune stimulating drug), treatments, protocols, or therapeutic regimens agents, a detectable response of any duration of time (long or short term), a desired outcome in or a benefit to a subject of any measurable or detectable degree or for any duration of time (e.g., for hours, days, months, years, or cured). The doses or "sufficient amount" or "effective amount" for treatment (e.g., to provide a therapeutic benefit or improvement) typically are effective to ameliorate a disorder, disease or condition, or one, multiple or all adverse symptoms, consequences or complications of the disorder, disease or condition, to a measurable extent, although reducing or inhibiting a progression or worsening of the disorder, disease or condition or a symptom, is considered a satisfactory outcome.

The term "ameliorate" means a detectable objective or subjective improvement in a subject's condition. A detectable improvement includes a subjective or objective reduction in the occurrence, frequency, severity, progression, or duration of a symptom caused by or associated with a disorder, disease or condition, an improvement in an underlying cause or a consequence of the disorder, disease or condition, or a reversal of the disorder, disease or condition.

Treatment can therefore result in inhibiting, reducing or preventing a disorder, disease or condition, or an associated symptom or consequence, or underlying cause; inhibiting, reducing or preventing a progression or worsening of a disorder, disease, condition, symptom or consequence, or underlying cause; or further deterioration or occurrence of one or more additional symptoms of the disorder, disease condition, or symptom. Thus, a successful treatment outcome leads to a "therapeutic effect," or "benefit" or inhibiting, reducing or preventing the occurrence, frequency, severity, progression, or duration of one or more symptoms or underlying causes or consequences of a condition, disorder, disease or symptom in the subject. Treatment methods affecting one or more underlying causes of the condition, disorder, disease or symptom are therefore considered to be beneficial. Stabilizing or inhibiting progression or worsening of a disorder or condition is also a successful treatment outcome.

A therapeutic benefit or improvement therefore need not be complete ablation of any one, most or all symptoms, complications, consequences or underlying causes associated with the condition, disorder or disease. Thus, a satisfactory endpoint is achieved when there is an incremental improvement in a subject's condition, or a partial reduction in the occurrence, frequency, severity, progression, or duration, or inhibition or reversal, of one or more associated adverse symptoms or complications or consequences or underlying causes, worsening or progression (e.g., stabilizing one or more symptoms or complications of the condition, disorder or disease), of one or more of the physiological, biochemical or cellular manifestations or characteristics of the disorder or disease, over a short or long duration of time (hours, days, weeks, months, etc.).

An amount sufficient or an amount effective can but need not be provided in a single administration and, can but need not be, administered alone or in combination with another composition (e.g., chemotherapeutic or immune stimulating agent), treatment, protocol or therapeutic regimen. For example, the amount may be proportionally increased as indicated by the need of the subject, status of the disorder, disease or condition treated or the side effects of treatment. In addition, an amount sufficient or an amount effective need not be sufficient or effective if given in single or multiple doses without a second composition (e.g., chemotherapeutic or immune stimulating agent), treatment, protocol or therapeutic regimen, since additional doses, amounts or duration above and beyond such doses, or additional compositions (e.g., chemotherapeutic or immune stimulating agents), treatments, protocols or therapeutic regimens may be included in order to be considered effective or sufficient in a given subject. Amounts considered sufficient also include amounts that result in a reduction of the use of another treatment, therapeutic regimen or protocol.

An amount sufficient or an amount effective need not be effective in each and every subject treated, prophylactically or therapeutically, nor a majority of treated subjects in a given group or population. As is typical for treatment or therapeutic methods, some subjects will exhibit greater or less response to a given treatment, therapeutic regimen or protocol. An amount sufficient or an amount effective refers to sufficiency or effectiveness in a particular subject, not a group or the general population. Such amounts will depend in part upon the condition treated, such as the type or stage of undesirable, aberrant or abnormal cell proliferation or hyperproliferative disorder (e.g., a cancer, tumor, neoplasia or malignancy), or pathogen infected cell, the therapeutic effect desired, as well as the individual subject (e.g., the bioavailability within the subject, responsiveness of the subject, gender, age, etc.).

Particular non-limiting examples of therapeutic benefit or improvement for undesirable, aberrant or abnormal cell proliferation, such as a hyperproliferative disorder (e.g., a cancer, tumor, neoplasia or malignancy) or pathogen infected cells, include a reduction in size, mass or volume, inhibiting or preventing an increase in size, mass or volume, or increased numbers or metastasis of hyperproliferative cells (e.g., tumor cells, cancer cells, neoplastic cells, metastatic cells), or pathogen infected cells, a slowing or inhibition of worsening or progression, stimulating cell lysis or apoptosis, decreasing, reducing or inhibiting proliferation or numbers of the hyperproliferative cells, tumor cells, cancer cells, neoplastic cells, metastatic cells, or pathogen infected cells, or decreasing, reducing or inhibiting tumor or cancer metastasis, or stabilizing numbers of hyperproliferative cells (e.g., tumor cells, cancer cells, neoplastic cells, metastatic cells), or pathogen infected cells, reducing mortality, and prolonging lifespan of a subject. Thus, inhibiting or delaying an increase in size, mass, volume or metastasis (stabilization) can increase lifespan (reduce mortality) even if only for a few days, weeks or months, even though complete ablation of the cancer, tumor, neoplasia, malignancy or pathogen infected cells has not occurred.

A reduction in the occurrence, frequency, severity, progression, or duration of a symptom of undesirable, aberrant or abnormal cell proliferation, such as a hyperproliferative disorder (e.g., a cancer, tumor, neoplasia or malignancy), or pathogen infected cells, such as an improvement in subjective feeling (e.g., increased energy, appetite, reduced nausea, improved mobility or psychological well being, etc.), are all examples of therapeutic benefit or improvement. Adverse symptoms and complications associated with a hyperproliferative disorder (e.g., a cancer, tumor, neoplasia or malignancy) that can be reduced or decreased include, for example, pain, nausea, lack of appetite, lethargy and weakness.

For example, a sufficient or effective amount of cells in which LTbeta receptor agonist has been attached, conjugated or coupled to the membrane, or a LIGHT (p30 polypeptide) variant or polymorphic form, is considered as having a therapeutic effect if administration results in less chemotherapeutic drug, radiation, immunotherapy or pathogen therapy being required for treatment of undesirable, aberrant or abnormal cell proliferation, such as a hyperproliferative disorder (e.g., a cancer, tumor, neoplasia or malignancy) or pathogen infected cells.

The term "subject" refers to animals, typically mammalian animals, such as humans, non human primates (apes, gibbons, chimpanzees, orangutans, macaques), domestic animals (dogs and cats), farm animals (horses, cows, goats, sheep, pigs) and experimental animal (mouse, rat, rabbit, guinea pig). Subjects include animal disease models, for example, animal models of undesirable or aberrant cell proliferation, such as a hyperproliferative disorder (e.g., a cancer, tumor, neoplasia or malignancy) or pathogen infected cells for analysis or study in vivo.

Subjects appropriate for treatment include those having or at risk of having undesirable, aberrant or abnormal cells, such as tumor, cancer, neoplastic, malignant or metastatic cells, or pathogen infected cells, those undergoing as well as those who are undergoing or have undergone anti-tumor, anti-cancer, anti-neoplastic, anti-malignant or anti-metastatic cells, or anti-pathogen infected cells therapy, including subjects in remission. The invention is therefore applicable to treating a subject who is at risk of undesirable, aberrant or abnormal cells, a tumor, cancer, neoplastic, malignancy or metastasis, or pathogen infected cells or an associated complication, for example, due to reappearance or regrowth following a period of quiescence or remission.

"At risk" subjects typically have risk factors associated with undesirable or aberrant immune response, immune disorder or immune disease, development of hyperplasia (e.g., a cancer or tumor), or exposure to or contact with a pathogen. Risk factors include gender, lifestyle (diet, smoking), occupation (medical and clinical personnel, agricultural and livestock workers), environmental factors (carcinogen exposure), family history (autoimmune disorders, diabetes, etc.), genetic predisposition, exposure, etc. For example, subjects at risk for developing melanoma include excess sun exposure (ultraviolet radiation), fair skin, high numbers of naevi (dysplastic nevus), patient phenotype, family history, or a history of a previous melanoma. Subjects at risk for developing cancer can therefore be identified by lifestyle, occupation, environmental factors, family history, and genetic screens for tumor associated genes, gene deletions or gene mutations. Subjects at risk for developing breast cancer lack Brca1, for example. Subjects at risk for developing colon cancer have early age or high frequency polyp formation, or deleted or mutated tumor suppressor genes, such as adenomatous polyposis coli (APC), for example. Subjects at risk for immunodeficiency with hyper-IgM (HIM) have a defect in the gene TNFSF5, found on chromosome X at q26, for example. Susceptibility to autoimmune disease is frequently associated with MHC genotype. For example, in diabetes there is an association with HLA-DR3 and HLA-DR4.

Compositions, including cells in which LTbeta receptor agonist has been attached, conjugated or coupled to the membrane of the cell, LIGHT (p30 polypeptide) variants and polymorphic forms, can be administered to provide the intended effect as a single or multiple, for example, in an effective or sufficient amount. Exemplary dosages are administered on consecutive days, or alternating days or intermittently. Single or multiple doses can be administered on the same or consecutive days, alternating days or intermittently.

Compositions can be administered and methods may be practiced via systemic, regional or local administration, by any route. For example, cells in which LTbeta receptor agonist has been attached, or LIGHT (p30 polypeptide) variants and polymorphic forms, may be administered systemically, regionally or locally, intravenously, orally (e.g., ingestion or inhalation), intramuscularly, intraperitoneally, intradermally, subcutaneously, intracavity, intracranially, transdermally (topical), parenterally, e.g. transmucosally or rectally. Compositions and methods of the invention including pharmaceutical formulations can be administered via a (micro)encapsulated delivery system or packaged into an implant for administration.

The invention further provides cells in which LTbeta receptor agonist has been attached, conjugated or coupled to the membrane, LIGHT (p30 polypeptide) variants and polymorphic forms, and LIGHT (p30 polypeptide) chimeras, included in pharmaceutical compositions and formulations. A pharmaceutical composition refers to "pharmaceutically acceptable" and "physiologically acceptable" carriers, diluents or excipients. As used herein, the term "pharmaceutically acceptable" and "physiologically acceptable," when referring to carriers, diluents or excipients includes solvents (aqueous or non-aqueous), detergents, solutions, emulsions, dispersion media, coatings, isotonic and absorption promoting or delaying agents, compatible with pharmaceutical administration and with the other components of the formulation. Such formulations can be contained in a tablet (coated or uncoated), capsule (hard or soft), microbead, emulsion, powder, granule, crystal, suspension, syrup or elixir.

Pharmaceutical compositions can be formulated to be compatible with a particular route of administration. Compositions for parenteral, intradermal, or subcutaneous administration can include a sterile diluent, such as water, saline solution, fixed oils, polyethylene glycols, glycerine, propylene glycol or other synthetic solvents. The preparation may contain one or more preservatives to prevent microorganism growth (e.g., antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose).

Pharmaceutical compositions for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (e.g., glycerol, propylene glycol, and polyetheylene glycol), and suitable mixtures thereof. Fluidity can be maintained, for example, by the use of a coating such as lecithin, or by the use of surfactants. Antibacterial and antifungal agents include, for example, parabens, chlorobutanol, phenol, ascorbic acid and thimerosal. Including an agent that delays absorption, for example, aluminum monostearate and gelatin can prolonged absorption of injectable compositions.

For transmucosal or transdermal administration, penetrants appropriate to the barrier to be permeated are used in the formulation. Such penetrants are known in the art, and include, for example, for transmucosal administration, detergents, bile salts, and fusidic acid derivatives; for transdermal administration, ointments, salves, gels, or creams.

Additional pharmaceutical formulations and delivery systems are known in the art and are applicable in the methods of the invention (see, e.g., *Remington's Pharmaceutical Sciences* (1990) 18th ed., Mack Publishing Co., Easton, Pa.;

*The Merck Index* (1996) 12th ed., Merck Publishing Group, Whitehouse, N.J.; *Pharmaceutical Principles of Solid Dosage Forms*, Technonic Publishing Co., Inc., Lancaster, Pa., (1993); and Poznansky, et al., *Drug Delivery Systems*, R. L. Juliano, ed., Oxford, N.Y. (1980), pp. 253-315).

In accordance with the invention, there are provided, methods of producing a cell having an LTbeta receptor agonist attached, conjugated or coupled to the membrane of the cell (e.g., to a molecule present on the cell membrane, such as a polypeptide, or carbohydrate). In one embodiment, a method includes contacting a cell with LTbeta receptor agonist under conditions allowing binding between said cell and said LTbeta receptor agonist (e.g., via an intermediary molecule), thereby producing a cell having LTbeta receptor agonist attached, conjugated or coupled to the membrane of the cell. In a particular aspect, the LTbeta receptor agonist is not expressed from a nucleic acid in the cell that encodes the LTbeta receptor agonist, but rather is attached, conjugated or coupled to the membrane via a covalent or non-covalent bond. In another embodiment, a method includes contacting a cell with a LIGHT (p30 polypeptide) variant or polymorphic form under conditions allowing binding between the LIGHT (p30 polypeptide) variant or polymorphic form, thereby producing a cell having LIGHT (p30 polypeptide) variant or polymorphic form attached, conjugated or coupled to the membrane of the cell. In a particular aspect of this embodiment, the LIGHT (p30 polypeptide) variant or polymorphic form is expressed from a nucleic acid in the cell that encodes the LIGHT (p30 polypeptide) variant or polymorphic form.

In particular aspects, an LTbeta receptor agonist includes one or more of LIGHT (p30 polypeptide), LTalpha1 beta2, LTalpha2 beta1, LTbeta or an LTbeta receptor antibody, or a chimeric protein which comprises a binding portion, such as a ligand, receptor or antibody or antibody subsequence that binds to a molecule present on the cell membrane. In more particular aspects, LIGHT (p30 polypeptide) includes a full length amino acid sequence, an extracellular amino acid sequence of LIGHT (e.g., as set forth in SEQ ID NO:1), or a soluble form of LIGHT (e.g., LIGHTt66, or as set forth in SEQ ID NO:2). In additional particular aspects, LIGHT (p30 polypeptide) includes LIGHT (p30 polypeptide) amino acid sequence with reduced affinity for DcR3 (Decoy receptor 3) as compared to native wild type LIGHT (p30 polypeptide), a LIGHT (p30 polypeptide) amino acid sequence with greater affinity for LTβR or HVEM as compared to native wild type LIGHT (p30 polypeptide), or a LIGHT (p30 polypeptide) amino acid sequence with greater affinity for LTβR or HVEM and with reduced affinity for DcR3 (Decoy receptor 3) as compared to native wild type LIGHT (p30 polypeptide), for example, a LIGHT (p30 polypeptide) amino acid sequence selected from any one of SEQ ID NOs:3 to 10.

In further particular aspects, the cell is a hyperproliferative cell, a tumor cell, cancer cell, neoplastic cell, a metastatic cell or a pathogen infected cell, or the cells expresses a molecule selected from a tumor cell or a cancer cell antigen, a neoplastic cell or a metastatic cell antigen, a viral antigen, a bacterial antigen, a fungal antigen, or a parasite antigen. Cells may be eukaryotic, mammalian (e.g., human) cells, that may be dead or alive.

In additional particular aspects, the cell is contacted with a first moiety (e.g., biotin or a biotin derivative) followed by contact with a second moiety (e.g., avidin, neutravidin or streptavidin, or a derivative or amino acid variant thereof) thereby producing a molecule comprising a first moiety bound to the cell, and a second moiety bound to the first moiety, said moieties comprising an intermediary molecule.

In still further particular aspects, the LTbeta receptor agonist binding to the cell membrane occurs via binding to an antibody present on the cell membrane, the LTbeta receptor agonist binds to the cell membrane via cross-linking the LTbeta receptor agonist to a molecule (e.g., protein or carbohydrate) on the cell membrane.

The invention provides kits including a cell having an LTbeta receptor agonist attached, conjugated or coupled to the membrane, LIGHT (p30 polypeptide) variants or polymorphic forms, combination compositions and pharmaceutical formulations thereof, packaged into suitable packaging material. A kit optionally includes a label or packaging insert including a description of the components or instructions for use in vitro, in vivo, or ex vivo, of the components therein. Exemplary instructions include instructions for reducing or inhibiting proliferation of a cell, reducing or inhibiting proliferation of a hyperproliferating cell, reducing or inhibiting proliferation of a neoplastic, tumor or cancer cell, malignancy or metastasis, or pathogen infected cell, treating a subject having a hyperproliferative disorder, treating a subject having a metastatic or non-metastatic neoplasia, tumor, cancer, or malignancy, or pathogen infected cells.

The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits of the invention can include labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., floppy diskette, hard disk, ZIP disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer information, lot numbers, manufacturer location and date.

Labels or inserts can include information on a condition, disorder, disease or symptom for which a kit component may be used. Labels or inserts can include instructions for the clinician or for a subject for using one or more of the kit components in a method, treatment protocol or therapeutic regimen. Instructions can include dosage amounts, frequency or duration, and instructions for practicing any of the methods, treatment protocols or therapeutic regimes set forth herein. Exemplary instructions include instructions for treating undesirable, aberrant or abnormal cells, a hyperproliferative disorder or pathogen infected cells. Kits of the invention therefore can additionally include labels or instructions for practicing any of the methods of the invention described herein including treatment, detection, monitoring or diagnostic methods.

Labels or inserts can include information on any benefit that a component may provide, such as a prophylactic or therapeutic benefit. Labels or inserts can include information on potential adverse side effects, such as warnings to the subject or clinician regarding situations where it would not be appropriate to use a particular composition. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Invention kits can additionally include other components. Each component of the kit can be enclosed within an individual container and all of the various containers can be within a single package. Invention kits can be designed for cold storage. Invention kits can further be designed to contain host cells expressing peptides or antibodies of the invention, or that contain encoding nucleic acids. The cells in the kit can be maintained under appropriate storage conditions until the cells are ready to be used. For example, a kit including one or more cells can contain appropriate cell storage medium so that the cells can be thawed and grown.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a", "and," and "the" include plural referents unless the context clearly indicates otherwise. Thus, for example, reference to "a cell in which LTbeta receptor agonist has been attached, conjugated or coupled to the membrane" or a "LIGHT (p30 polypeptide) variant or polymorphic form" includes a plurality of such cells, variants or polymorphic forms, and so forth.

As used herein, all numerical values or numerical ranges include integers within such ranges and fractions of the values or the integers within ranges unless the context clearly indicates otherwise. Thus, for example, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example includes a description of various materials and methods.

Figure 12:
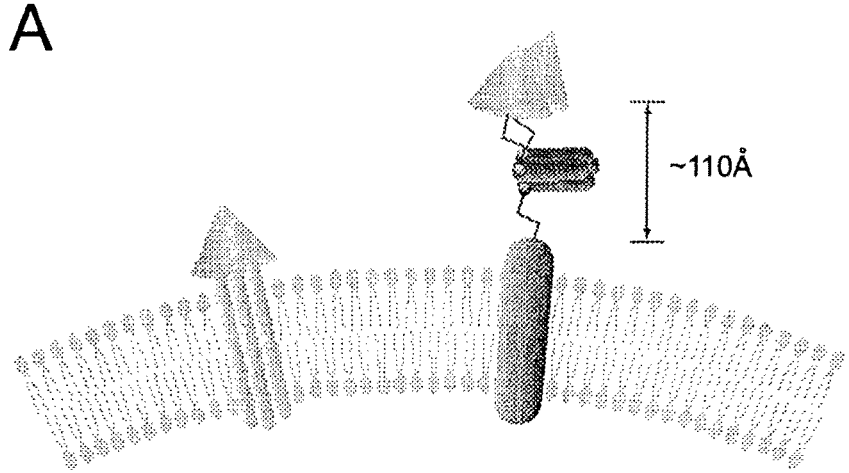
FIGS. 12A-12B. A biotin-based protein immobilization system. (A) Schematic illustration of native LIGHT and immobilization of soluble LIGHT. Native LIGHT trimer contains a transmembrane domain is shown on the left side. The immobilization of soluble LIGHT is shown on the right side. A representative cell surface molecule (protein) is shaded gray. Biotin derivative with linker is shown as a single gray line extending from the molecule. Neutravidin™ tetramer is shown as cylinders. Soluble human LIGHT (LIGHTt66) is shown as a trimer. (B) Schematic illustration of assembly of a LIGHT decorated cell. (B) Schematic illustration for the assembling of a LIGHT decorated cell. The cell surface of a target cell was modified with a biotin derivative, and the cells were washed with PBS to remove the free biotin. The cells were fixed with 1% formalin. Then the cells were incubated with Neutravidin™ (10 µg/ml) in PBS for 30 min, and the cells were washed to remove the free Neutravidin™. The cells were then incubated with biotinylated LIGHT (1 µg/ml) for 45 min, and the cells were washed to remove the unincorporated LIGHT.
Figure 12:
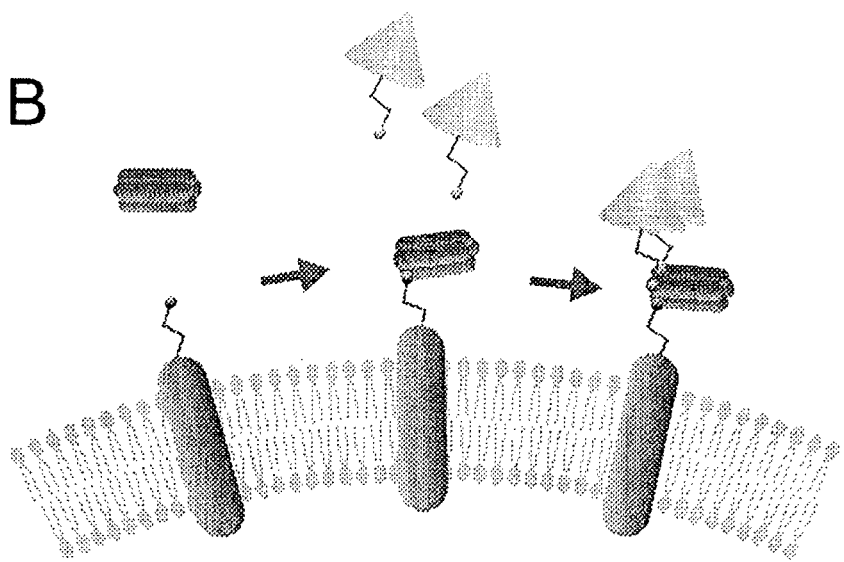

Biotin Based Immobilization of LIGHT on Tumor Cells:

A schematic illustration for the assembling of a LIGHT decorated cancer cells (FIG. 12) shows the procedure involves three successive steps: (i) biotinylation of cancer cells, (ii) biotinylation of soluble LIGHT, and (iii) immobilization of soluble LIGHT on the biotinylated cancer cells. Aseptic techniques are required throughout the procedures.

Biotinylation of Cancer Cells:

The source of cancer cells can be purified from wide variety of malignant tissues after tumor resection (Greiner, et al., J Lab Clin Med 109:244 (1987); and O'Brien, et al., Cytometry 28:81 (1997). In this preparation, we used EL4 cells. $50 \times 10^6$ of EL4 cells were washed 3 times with ice-cold Dulbecco's Phosphate Buffer Saline (PBS) pH 8.0 (Invitrogen Corporation, USA; Cat. #14190-144) to remove any contaminating proteins from the tissue culture media. The cells were equally divided into 2 tubes ($25 \times 10^6$ cells/tube), and were resuspended in 1 ml PBS (pH 8.0). A commercially available biotinylation reagent, NHS-PEO4-Biotin (Pierce, Ill., USA; Cat. #21329), was used in this labeling reaction. Immediately before use, 200 µl of ultrapure distilled water (Invitrogen Corporation, cat. #10977-015) was added to 2 mg of NHS-PEO4-Biotin, and 50 µl of the NHS-PEO4-Biotin solution was added to each tube containing $25 \times 10^6$ EL4 cells. The samples were incubated at room temperature for 30 minutes with intermittent mixing in every 5 minutes. The cells were then washed 3 times with 1 ml cold PBS (pH 8.0) to remove non-reacted biotinylation reagent. The prepared EL4 cells were fixed in 1% formalin (Protocol™, USA; Cat. #245-684) on ice for 30 minutes, washed for 4 times with 1.2 ml ice-cold PBS (pH 7.4), and stored at 4° C.

Biotinylation of Soluble LIGHT:

Purified soluble human LIGHT (LIGHTt66, concentration=0.262 mg/ml in PBS, pH 8.0) was used in the biotin labeling reaction (Rooney, et al. J. Biol. Chem. 275:14307 (2000)). Immediately before use, 200 µl of ultrapure distilled water (Invitrogen) was added to 2 mg of NHS-PEO4-Biotin, and 3.7 ml of the NHS-PEO4-Biotin solution was added to LIGHTt66. The sample was incubated on ice for 2 hours. Afterwards, 42 µl of 1 M Tris (pH 8.0) (Fisher Scientific, USA; Cat. # BP154-1) was added to stop the reaction. The sample was dialyzed against 1 liter of PBS with buffer exchanged three times. The biotinylated LIGHTt66 was sterilized by filtering through a 0.22 mm Millex-GV filter (Millipore, Ireland, Cat. # SLGV004SL), subdivided into small aliquots, and stored in −80° C.

Immobilization of Soluble LIGHT on the Biotinylated Cancer Cells:

Biotinylated and formalin fixed EL4 cells ($30 \times 10^6$) were used in this preparation. The cells were resuspended in 1 ml PBS (pH 7.4) and were incubated with 10 µg/ml of Neutravidin™ (Pierce; Cat. #31000) for 30 minutes. The cells were washed 4 times with 1 ml ice-cold PBS (pH 7.4) to remove the free Neutravidin™. The cells were then incubated with biotinylated LIGHTt66 (1 µg/ml) for 45 minutes and washed 3 times with 1 ml ice-cold PBS (pH 7.4) to remove the unincorporated LIGHT. The prepared cells were resuspended in sterile PBS ($40 \times 10^6$ cells/ml) and stored in 4° C. for in vivo anti-tumor studies.

Example 2

This example shows data demonstrating suppression of tumor growth by expressing LIGHT on the surface of tumor cells.

To analyze the efficacy of LIGHT mediating tumor rejection, the EL4 tumor model was used. EL4 is a mouse thymoma cancer cell line derived from C57/BL6 (B6) mouse. When EL4 cells were injected subcutaneously into syngeneic B6 mouse, a solid tumor develops in 5 to 7 days and progresses to a lethal tumor typically by 15-20 days. Human LIGHT as a potential immunotherapeutic was used. An EL4 cell line stably expressing LIGHT was made using recombinant retrovirus. Human LIGHT expressing EL4 cells (EL4-LIGHT) were injected subcutaneously into syngeneic B6 mice, and the growth of the tumor was monitored. The average tumor size achieved between the control (7.5 cm$^3$) and the test group over a 15-20 day time frame was significantly different (p<0.05) (FIG. 1A). A massive tumor grew in mice injected with EL4 cells that were transduced with control empty vector (EL4-V). In contrast, in mice injected with EL4-LIGHT cells tumors did not grow and thus were rejected. This result demonstrates that human LIGHT induced anti-tumor responses when expressed in mouse tumor cells.

To determine if unmodified EL4 cells would grow in the presence of LIGHT-expressing EL4 cells, equal numbers of EL4-V and EL4-LIGHT cells were separately injected in the same mouse. EL4-V cells were used as a control (FIG. 1B). In mice injected with EL4-V cells, the tumor grew rapidly. For the co-injection group, the presence of LIGHT-expressing EL4 cells triggered the rejection of the non-LIGHT expressing EL4 tumor at the distal location, showing a systemic effect of tumor rejection. This result is important for two reasons. First, it shows that the tumor rejection was not due to the present of a human protein because the EL4-V cells, which did not have LIGHT, were also rejected. Second, the results demonstrated that LIGHT expressing EL4 cells were capable of mediating a systemic response against the EL4 tumor.

Example 3

This example shows the effect of the LIGHT isoform in stimulating anti-tumor responses.

In human and mouse, there exist at least three major isoforms of LIGHT (membrane LIGHT, soluble LIGHT and LIGHTΔTM)(Granger, et al., J Immunol 167:5122 (2001). Membrane LIGHT represents the full-length form of LIGHT with a transmembrane anchor. Membrane LIGHT can be shed (proteolytically cleaved on the outside of the cell), into a soluble form, and the third isoform of LIGHT is formed by alternate splicing, generating a deletion of the transmembrane domain (LIGHTΔTM). LIGHTΔTM lacks the transmembrane domain and is located to the cytosol.

To determine if these other isoforms of LIGHT induce anti-tumor responses, EL4 cell lines that stably express a soluble form of LIGHT (EL4-LIGHTt66) and LIGHTΔTM (EL4-LIGHTΔTM) were made using recombinant retroviruses. These cell lines were injected into two groups of mice and the growth of tumor monitored. The results (FIG. 2A) establish that cells expressing either soluble LIGHT or LIGHTΔTM were unable to induce an anti-tumor response.

Figure 2:
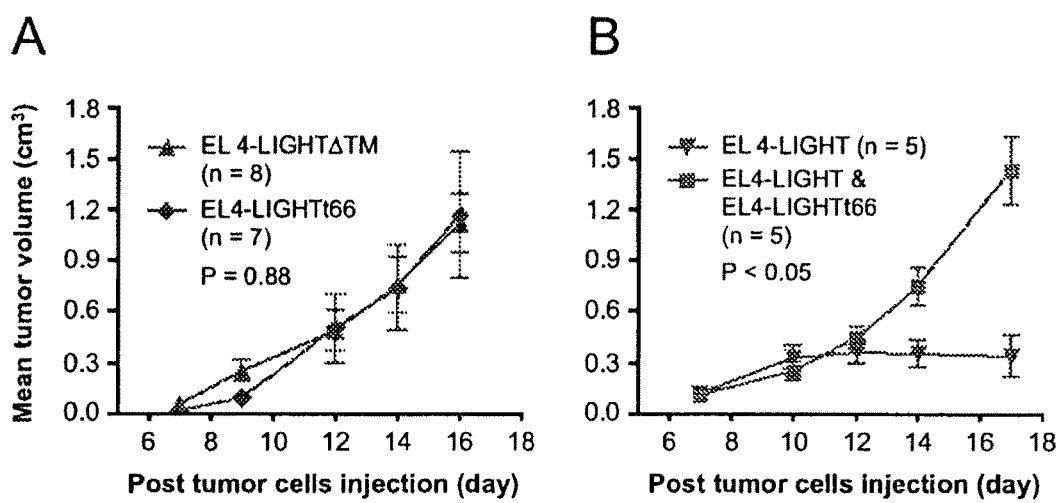
FIGS. 2A-2B. The effect of LIGHT isoforms on LIGHT-mediate anti-tumor responses. (A) EL4-LIGHTΔTM or EL4-LIGHTt66 were injected subcutaneously with $2.5 \times 10^5$ cells per mouse in each group. Tumor growth was measured over a period of 17 days. (B) EL4-LIGHT ($1.25 \times 10^5$ cells) and EL4-LIGHTt66 ($1.25 \times 10^5$ cells) were mixed and injected per mouse. EL4-LIGHT ($2.5 \times 10^5$ cells) were injected to a separate group as control. Note that the presence of EL4-LIGHT-t66 strongly inhibited the anti-tumor responses mediated by cells expressing membrane LIGHT.

To determine if soluble LIGHT impairs tumor rejection mediated by EL4-LIGHT, a mixture of EL4-LIGHT and EL4-LIGHTt66 were injected into B6 mice and the tumor growth was monitored (FIG. 2B). Mice injected with EL4-LIGHT cells showed a complete loss of tumor growth. In contrast, in mice injected with both EL4-LIGHT and EL4-soluble LIGHT tumors grew rapidly. Thus, soluble LIGHT impaired LIGHT-dependent anti-tumor responses. These results indicate that membrane bound LIGHT is essential for LIGHT-mediated anti-tumor activity.

Example 4

This example includes a description of a biotin-based protein immobilization system.

Viral and bacterial based vector delivery systems in humans have inherent safety issues. To circumvent these inherent issues with vector-based delivery systems, a biochemical-based approach, independent of vectors, was developed to attach functional LIGHT to the surface of tumor cells. The procedure is an immobilization system to display soluble proteins on virtually any cell surface in a stable format using a chemical (biotin) linkage. This method (illustrated in FIGS. 3A and B) used purified recombinantly expressed soluble LIGHT (LIGHTt66) (Rooney, et al., J. Biol. Chem. 275:14307 (2000)) and EL4 tumor cells for enhanced immunity. First, the cell surface proteins on EL4 cells were biotinylated. Second, soluble LIGHT (LIGHTT66) was also biotinylated. Biotinylated soluble LIGHT was immobilized to the biotinylated EL4 cell membrane proteins through addition of tetrameric Neutriavidin. Since the binding between biotin and Neutriavidin is very strong, this biotin-Neutriavidin-biotin complex is extremely stable in vivo.

Figure 3:
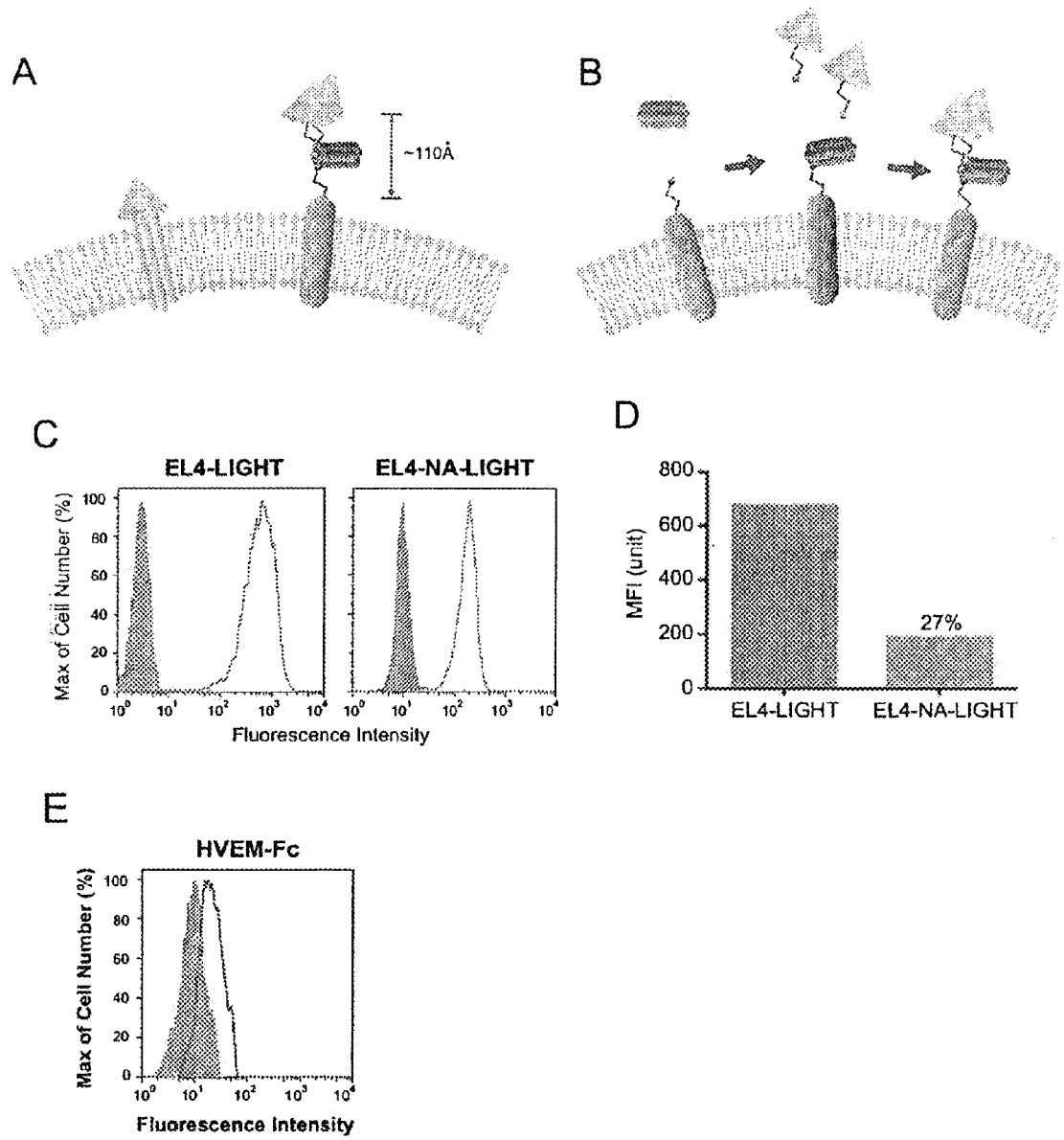
FIGS. 3A-3E. Biotin-based protein immobilization system. Schematic illustration of (A) native LIGHT (traversing the membrane bilayer) and immobilization of soluble LIGHT. A representative cell surface molecule (protein) is shaded gray. Biotin derivative with linker is shown as a single gray line extending from the molecule. Neutravidin™ tetramer is shown as cylinders. Soluble human LIGHT (LIGHTt66) is shown as a trimer. (B) Schematic illustration of assembly of a LIGHT decorated cell. The cell surface of a target cell was modified with a biotin derivative, and cells were washed with PBS to remove free biotin. The cells were fixed with 1% formalin, incubated with Neutravidin (10 μg/ml) in PBS for 30 min, and subsequently washed to remove free Neutravidin. Cells were then incubated with biotinylated LIGHT (1 μg/ml) for 45 min, and washed to remove the unincorporated LIGHT. (C) Staining for cell surface LIGHT on LIGHT-decorated EL4 cells. EL4-NA-LIGHT (blue line) and EL4-NA (shad of gray) cells were incubated with human anti-hLIGHT recombinant "Omniclone" antibody (5 μg/ml) in binding buffer (PBS with 2% FCS) for 60 min, washed and stained with PE conjugated goat anti-human IgG (Southern Biotech) and fluorescence detected by flow cytometry. Cells transduced with retrovirus expressed EL4-LIGHT (green line) and EL4-V (shade of gray) cells were used as controls. (D) Efficiency of immobilization. The specific mean fluorescence intensity (MID of the surface LIGHT staining between EL4-LIGHT and EL4-NA-LIGHT as in (C) was determined. (E) Binding of mouse HVEM to EL4-NA-LIGHT cells. Cells were incubated with mouse HVEM-Fc (20 μg/ml) in binding buffer (PBS with 2% FBS) for 60 min, washed and stained with PE conjugated goat anti-human IgG (Southern Biotech) and fluorescence detected by flow cytometry (line). The parental EL4-NA cells were used as negative control (shade of gray).

To determine the efficiency of immobilization, LIGHTt66 was detected by flow cytometry and EL4-LIGHT cells were used for comparison. Immobilized soluble LIGHT on the surface of EM cells was detected by antibody staining or with HVEM-Fc (FIGS. 3C, E). Surrogate receptors for LIGHT, LTβR-Fc and HVEM-Fc were prepared as described (Rooney, et al., Methods Enzymol 322:345 (2000)).

The fluorescence intensity of the LIGHT-decorated EL4 cells (EL4-NA-LIGHTt66) was 27% of the level expressed by retrovirus transduced EL4 cells (EL4-LIGHT) (FIG. 3D) indicating that the method can deliver LIGHT to cell membrane comparable to retrovirus transduction. The results demonstrate that this biotin-based immobilization system is an effective way to attach purified LIGHT to the surface of cells, such as tumor cells. Thus, this biotin-based immobilization system serves as an example that biologically active LTbeta receptor agonists such as LIGHT can be attached or coupled to tumor cell surface. This biotin-based cell membrane immobilization system is a viable non-vector based alternative for modifying tumor cells with LTbeta receptor agonists such as LIGHT in order to enhance immune responses against tumor cells when cells are administered to animals.

Example 5

This example includes data demonstrating suppression of tumor growth by EL4 cells having LIGHT attached, coupled or conjugated to the cell membrane.

Figure 4:
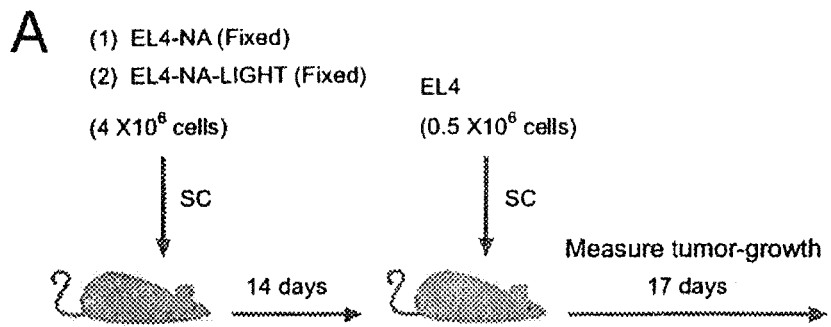
FIGS. 4A-4C. Suppression of tumor growth by preimmunization with LIGHT decorated cancer cells. (A) Schematic illustration of the design for LIGHT dependent tumor vaccination. Formalin fixed Neutravidin decorated EL4 (EL4-NA) cells ($4 \times 10^6$) or human LIGHT-Neutravidin decorated EL4 (EL4-NA-LIGHT) cells were injected subcutaneously into B6 mice (n=4 or 5 mice). After 14 days, these mice were challenged with live EL4 cells ($0.5 \times 10^6$ cells per mouse). Tumor growth was measured over 17 days. (B) Formalin fixed human LIGHT-Neutravidin decorated EL4 (EL4-NA-LIGHT) cells ($4 \times 10^6$) or Neutravidin decorated EL4 (EL4-NA) cells ($4 \times 10^6$) were injected subcutaneously (SC) into B6 mice (n=5 mice per group). After 14 days, serum was collected from mice in each group, and mouse antibody activity bound to unmodified EL4 cells was measured by flow cytometry. Unmodified EL4 cells were incubated with serum (1:5 dilution) in 40 μl of binding buffer for 60 min, washed, and stained with goat anti-mouse IgG-PE secondary antibody, and fluorescence was detected by flow cytometry. Mice preinjected with EL4-NA cells did not generate detectable anti-EL4 antibody activity. However, anti-EL4 antibody responses were detected in 3 of 4 mice preimmunized with EL4-NA-LIGHT cells. (C) The effect of preinjected EL4-NA-LIGHT cells on challenged EL4 tumor growth.
Figure 4:
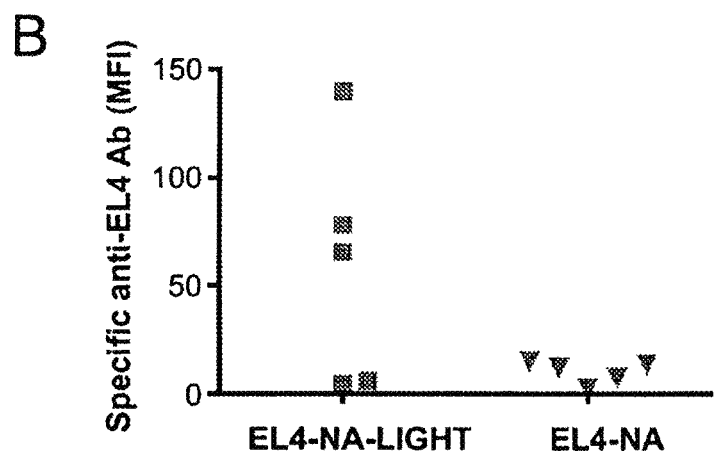
Figure 4:
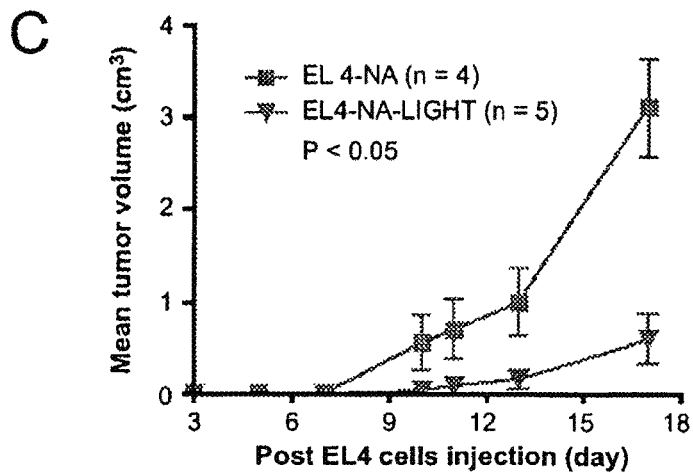

To ascertain the ability of LIGHT decorated cells to function as a cancer vaccine, a protocol was designed to evaluate efficacy of LIGHT conjugated EL4 cells as cancer vaccine (FIG. 4A). Two groups of mice were injected with formalin fixed EL4 cells either conjugated to LIGHTt66 (EL4-NA-LIGHTt66) or conjugated to Neutravidin (EL4-NA). Mice were injected with EL4-NA-LIGHTt66 or EL4-NA cells 14 days prior to injection with viable EL4 tumor cells in order to generate an immune response, as in a typical vaccine strategy. To examine the induction of humoral immunity by LIGHT-decorated EL4 cells, pre- and postimmune sera were collected from each group of mice and tested for anti-EL4 antibody activity by flow cytometry using unmodified EL4 cells (FIG. 4B). Mice vaccinated with EL4-NA cells did not generate detectable anti-EL4 activity. In contrast, anti-EL4 antibody activity was detected in sera of 3 of 5 mice that were injected with EL4-NA-LIGHT, demonstrating that immunization with LIGHT-decorated EL4 cells elicited antibody responses to EL4 antigens.

To determine efficacy of LIGHT decorated EL4 cells as an immune enhancing vaccine, EL4 cells were injected in each group and tumor growth was monitored. The mice immunized with LIGHTt66-decorated EL4 cells showed a significant reduction in tumor growth rate (FIG. 4C). These data demonstrate immunization with LIGHT-decorated EL4 cells generates an immune response against the EL4 tumor that inhibits tumor progression.

Example 6

This example includes data demonstrating suppression of primary tumor growth with EL4 cells having LIGHT attached, coupled or conjugated to the cell membrane.

Figure 5:
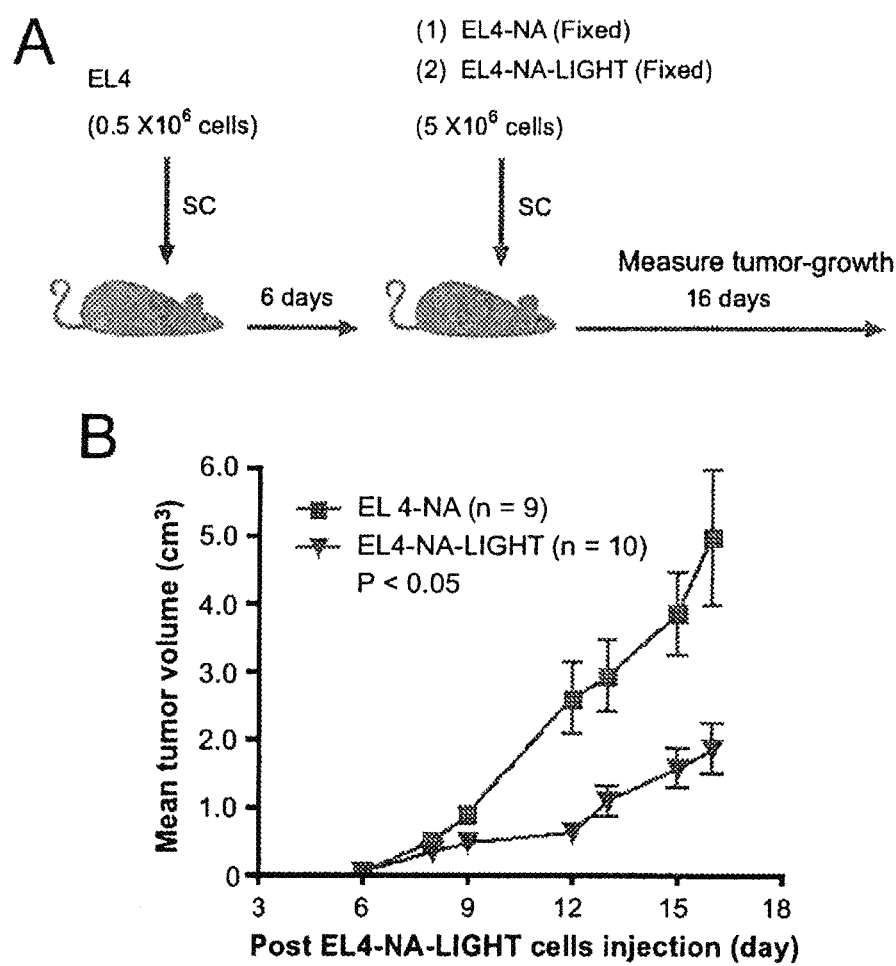
FIGS. 5A-5B. Suppression of primary tumor growth with LIGHT decorated cancer cells. (A) Schematic illustration of the study design. Viable EL4 cells ($0.5 \times 10^6$) were inoculated subcutaneously (SC) into B6 mice (n=19) and tumor allowed to grow to a palpable thickening was observed (typically 6 days). Formalin fixed LIGHT decorated EL4 cells ($0.5 \times 10^6$) were injected on day 6 into the tumor mass. The formalin fixed Neutravidin decorated EL4 cells were used as a control. (B) The effect of vaccinating with EL4-NA-LIGHT cells on an established EL4 tumor.

To evaluate the ability of LIGHT-decorated EL4 cells to inhibit growth of a primary tumor, EL4 cells were injected into mice subcutaneously and the cells were allowed to proliferate so a pre-established tumor was formed. Then, formalin fixed EL4-NA-LIGHT cells were injected into tumor area, and tumor growth was monitored for an additional 16 days (FIG. 5A). Formalin fixed EL4-NA was used as control.

Mice injected with EL4-NA-LIGHT cells showed a reduction of tumor growth compared to the EL4-NA control. These results demonstrate the efficacy of LIGHT-decorated EL4 cells to suppress growth of an established tumor. Tumor cells having attached, conjugated or coupled LTbeta receptor agonists such as LIGHT are therefore also useful as treatments of established tumors (FIG. 5B).

Example 7

This example includes data demonstrating receptor requirement for LIGHT-mediated anti-tumor responses.

To gain molecular insight into LIGHT-mediated anti-tumor response, receptor requirement for LIGHT-mediated anti-tumor activity was evaluated. LIGHT can interact with 2 signaling receptors, HVEM and LTβR. To determine which of these two receptors were required for LIGHT-mediated anti-tumor responses, analysis of tumor rejection in LTβR and HVEM knockout (KO) mice was performed.

Figure 6:
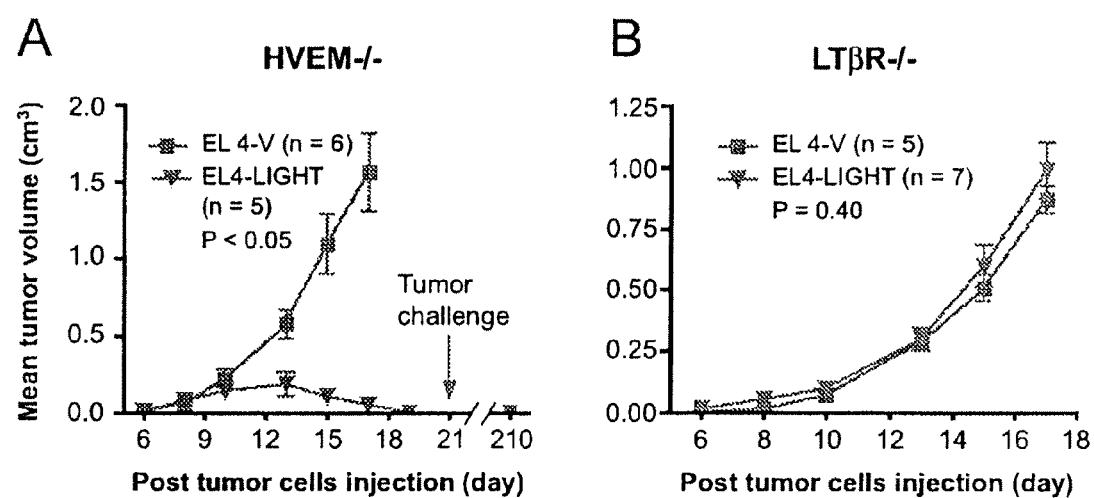
FIGS. 6A-6B. Receptor requirement for LIGHT-mediated anti-tumor responses. EL4-LIGHT cells ($2.5 \times 10^5$ cells per mouse) were injected subcutaneously into mice deficient in (A) hvem, (B) ltβr. Mice deficient in LTβR could not reject EL4-LIGHT tumor.

In HVEM KO mice, EL4-LIGHT cells were rejected (FIG. 6A), suggesting that HVEM was not essential for LIGHT-mediated anti-tumor responses. When these mice were later challenged with parental EL4 cells, no tumor developed. In contrast, in LTβR KO mice, EL4 tumors were not rejected, indicating that LIGHT signaling through LTβR participates in LIGHT-mediated anti-tumor activity (FIG. 6B).

Example 8

This example includes data demonstrating that LIGHT stimulates CCL21 production in tumor environment.

Figure 7:
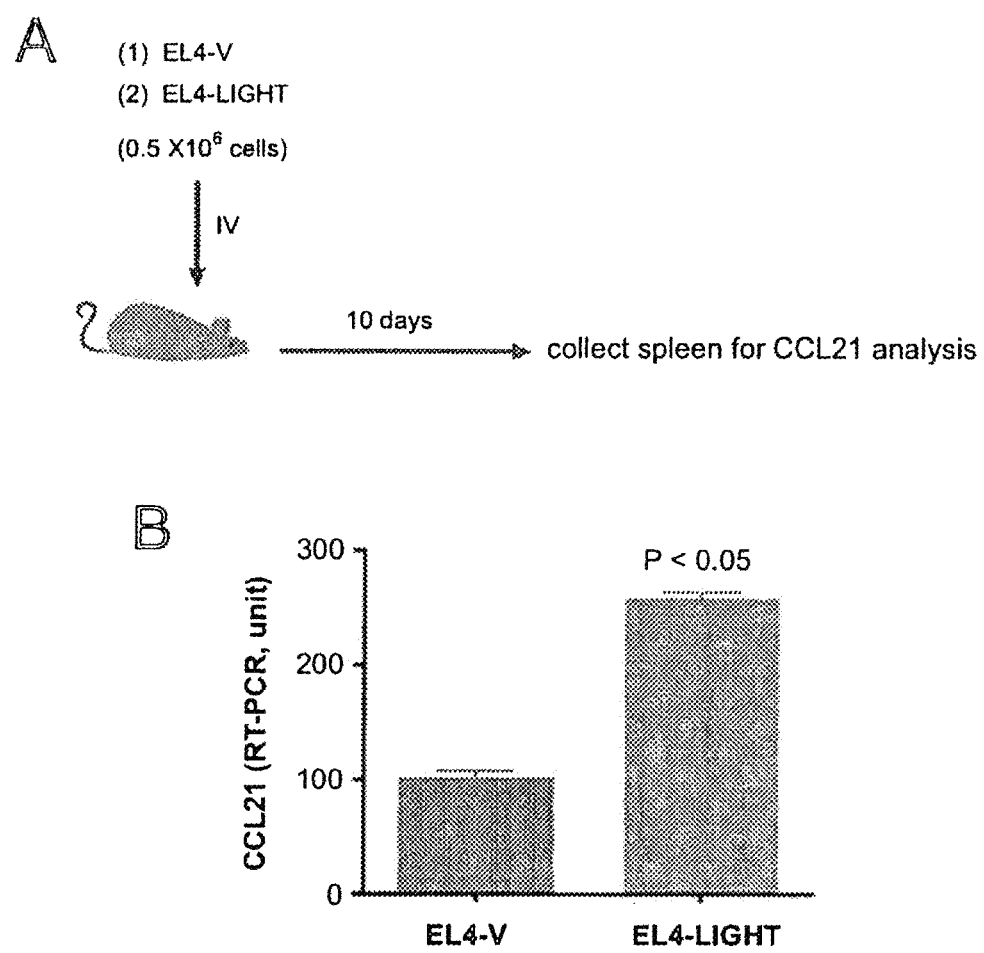
FIGS. 7A-7B. Induction of CCL21 by EL4-LIGHT cells in the tumor environment. (A) Schematic illustration of the study design for CCL21 analysis in the tumor environment. EL4-V or EL4-LIGHT cells were injected intravenously into B6 mice. Spleens were collected 10 days later for RT-PCR analysis of chemokine CCL21. (B) In mice injected with EL4-LIGHT there was a 2.5 fold increase in CCL21 expression in the tumor-infiltrated spleen compared to mice injected with the EL4-V control.

ETA-LIGHT cells when injected into recombinase activating gene-2 (RAG2$^{-/-}$) mice, which lack T and B cells, through the intravenous route, were detected in spleen, liver and lung. To examine the ability of LIGHT to stimulate chemokines in tumor environment, ETA-LIGHT cells were injected into RAG2$^{-/-}$ mice and spleens were collected for the detection of CCL21 using real time RTPCR (FIG. 7A). Mice injected with ETA-LIGHT exhibited a 2.5 fold increase in CCL21 expression compared to mice injected with ETA cells as control (FIG. 7B). This result demonstrates that LIGHT in the tumor environment increases CCL21 production in the absence of T and B cells.

Example 9

This example includes a discussion of data indicating a mechanism of LIGHT-mediated anti-tumor activity.

LTβR interacts with LIGHT, LTβ, and LTα1β2. To examine the contribution of endogenous LIGHT, LTβ and LTα to LIGHT-meditated anti-tumor activity, EL4-LIGHT cells were injected subcutaneously into mice genetically deficient in one or more of the cellular ligands of the LTβR (LIGHT$^{-/-}$LTβ$^{-/-}$, LIGHT$^{-/-}$, LTβ$^{-/-}$, and LTα$^{-/-}$).

Figure 8:
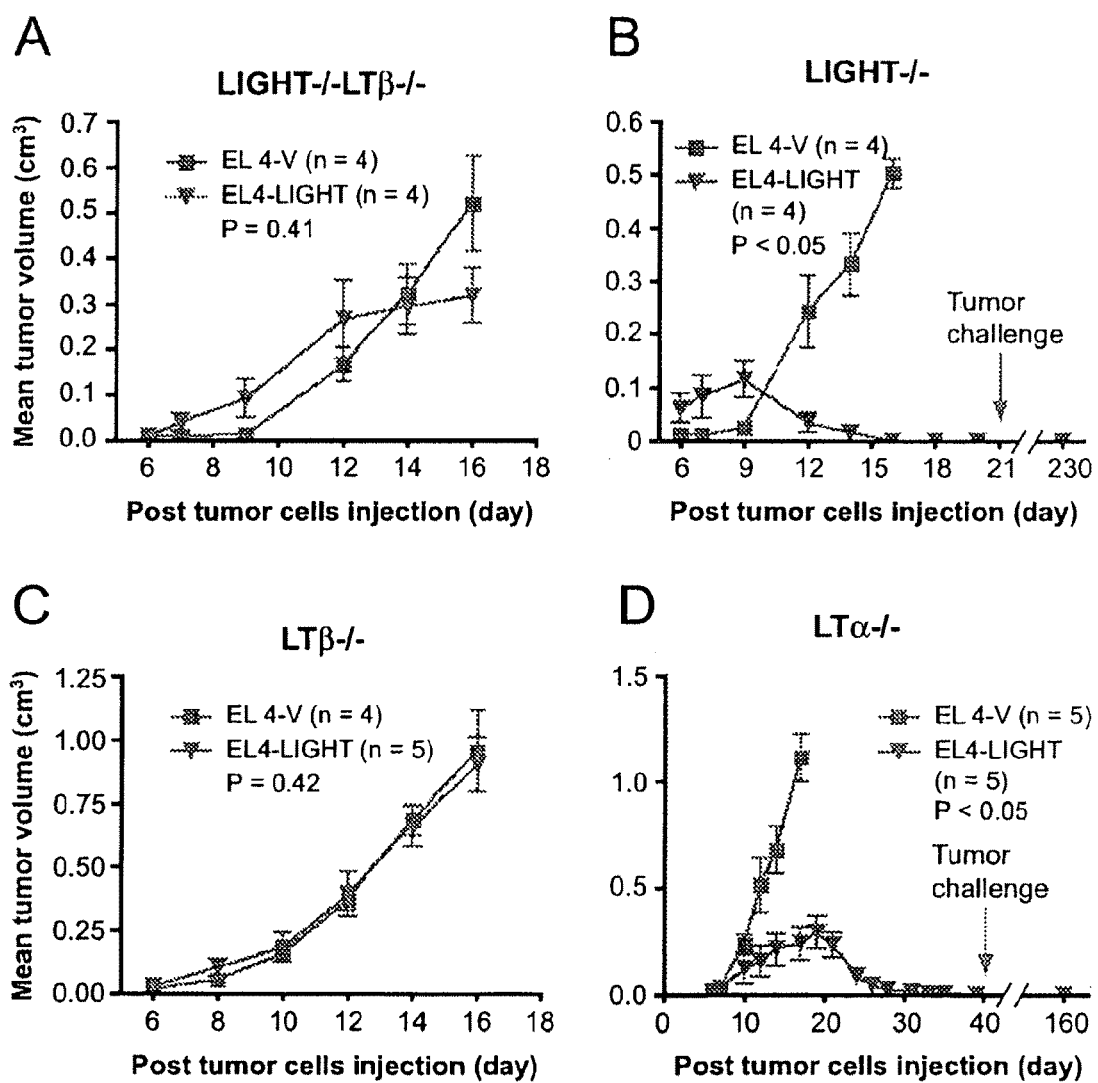
FIGS. 8A-8D. Ligands required for LIGHT-mediated anti-tumor responses. EL4-LIGHT cells ($2.5 \times 10^5$ cells per mouse) were injected subcutaneously into mice genetically deficient in (A) both light and ltβ (B) light, (C) ltβ or (D) ltα. Tumor growth was measured over a period of 16-39 days. Mice deficient in $LT\beta^{-/-}$ (C) were not able to reject EL4-LIGHT tumors, indicating that LTβ participates in LIGHT-mediated anti-tumor responses.

In mice deficient in both LIGHT$^{-/-}$ and LTβ$^{-/-}$, ETA-LIGHT tumors were not rejected, suggesting that endogenous LIGHT and/or LTβ participate in LIGHT-mediated anti-tumor activity (FIG. 8A). However, when ETA-LIGHT cells were injected into LIGHT$^{-/-}$ mice, the tumor was rejected, indicating that endogenous LIGHT was not required for tumor control. When these mice were later challenged with parental ETA cells, the tumor was still rejected (FIG. 8B).

To determine if lymphotoxin participates in tumor rejection, EL4-LIGHT cells were injected into LTβ$^{-/-}$ or LTα$^{-/-}$ mice (FIGS. 8C and D). Mice deficient in LTβ were not able to reject the ETA-LIGHT tumor, indicating that LTβ participates in LIGHT-mediated tumor control. In contrast, the ETA-LIGHT tumor was rejected in the LTα$^{-/-}$ mice, although it required a longer time for the process of rejection, suggesting that LTα may contribute to but was not essential for LIGHT-mediated tumor control.

EL4-LIGHT cells were capable of inducing anti-tumor responses in the absence of secondary lymphoid organs which are missing in the LTα$^{-/-}$ mice. Furthermore, LTα$^{-/-}$ mice served as a phenotypic control for the other mutant mice lacking secondary lymphoid organs such as LTβR$^{-/-}$ (FIG. 6B) and LTβ$^{-/-}$ (FIG. 8C). Mice deficient in LIGHT$^{-/-}$ or LTα$^{-/-}$, which rejected EL4-LIGHT tumors, when subsequently challenged with unmodified EL4 cell, showed no tumor formation (FIGS. 8B and D) and these mice remained tumor free of tumors for >5 months, indicating a sustained memory response to the EL4 tumor was induced by the treatment.

Example 10

This example includes data indicating that expression of LTβ in T and B lymphocytes contributes to LIGHT-mediated anti-tumor activity.

Figure 9:
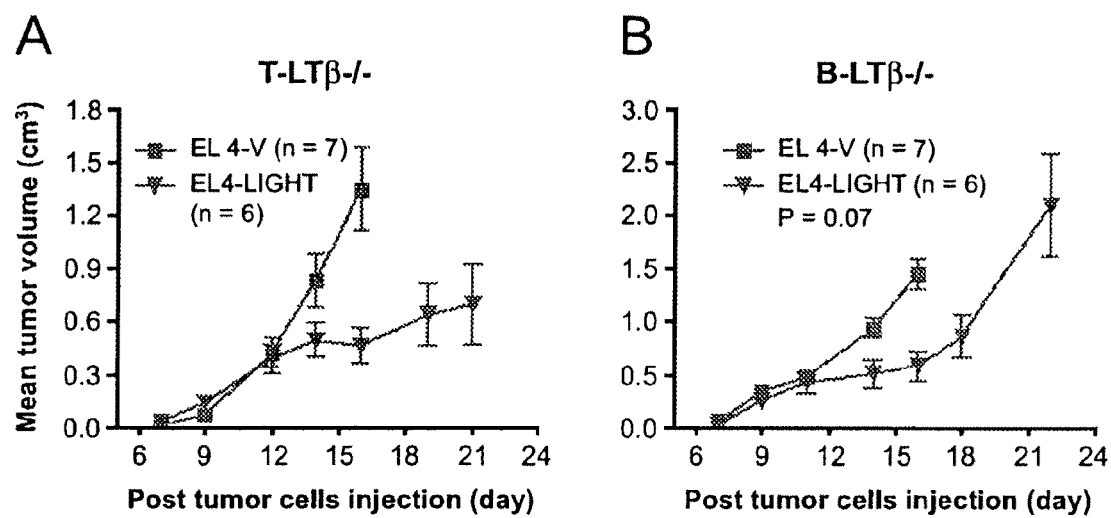
FIGS. 9A-9B. LTβ expression in T and B cells is essential for LIGHT-mediated anti-tumor responses. EL4-LIGHT cells ($2.5 \times 10^5$) were injected subcutaneously into mice conditionally deleted for ltβ in: (A) T cells (T-$LT\beta^{-/-}$), or (B) B cells (B-$LT\beta^{-/-}$). Tumor growth was measured over a period of 21-22 days. Mice deficient in LTβ in the T or B cell compartment were not able to reject EL4-LIGHT tumors, indicating that the expression of LTβ in both T or B cell compartments was essential, but not sufficient, for LIGHT-mediated anti-tumor responses.

To further investigate the cellular requirement for LTβ expression for LIGHT-mediated tumor rejection, conditional knock out mice with LTβ specifically deleted in either T cells (T-LTβ$^{-/-}$) or B cells (B-LTβ$^{-/-}$) were used as a host to examine the immunostimulating effect of EL4-LIGHT. EL4-LIGHT cells were injected subcutaneously into T-LTβ$^{-/-}$ and B-LTβ$^{-/-}$ mice, and tumor growth was monitored for 22 days. Mice deficient in ltβ in either T or B cells were unable to reject the EL4-LIGHT tumor. This data indicates that both T or B cell expression of LTβ participates in LIGHT-mediated tumor rejection (FIG. 9).

Example 11

This example includes a description of variant forms of LIGHT that can enhance immunotherapy.

Figure 10:
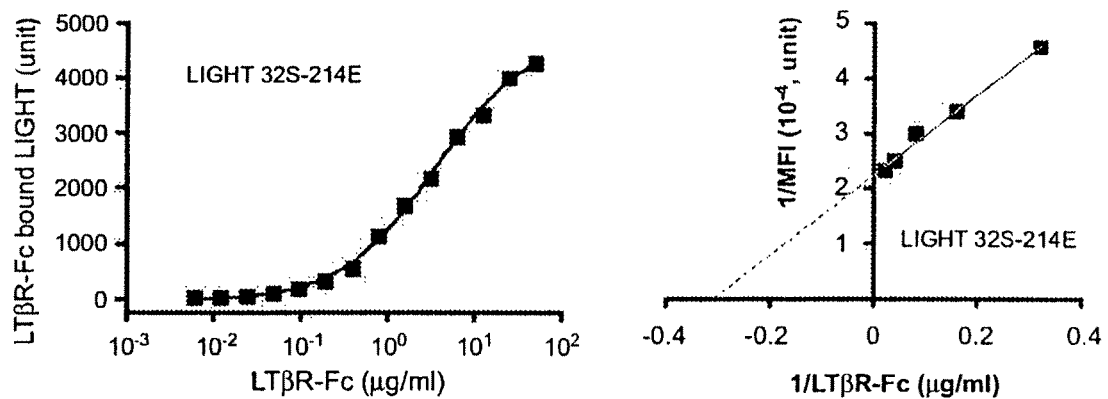
FIGS. 10A-10E. Affinity of LTβR-Fc, HVEM-Fc and DcR3-Fc for variant forms of human LIGHT. (A) EL4 cells stably expressing the predominant form of LIGHT (32S-214E) were incubated with graded amount of LTβR-Fc (3 ng to 50 µg/ml) in 100 µl of binding buffer for 60 min, washed and stained with PE conjugated goat anti-human IgG and fluorescence detected by flow cytometry. Specific mean fluorescence intensity (MFI) was obtained by subtracting the background fluorescence staining of the parental EL4 cells (negative control) from the experimental group. Equilibrium binding constants were calculated by nonlinear regression analysis using Prism GraphPad (v4; San Diego, USA) (left panel) and double reciprocal plot (right panel). Binding of LIGHT variants 32S-214K (B) and 32L-214E to LTβR-Fc were examined as in (A). (D) EL4 cells stably expressing various polymorphic forms of LIGHT (32S-214E, 32S-214K, and 32L-214E) were examined their binding avidity to LTβR-Fc, HVEM-Fc and DcR3-Fc using flow cytometry based assay as in (A). (E) EL4 cells stably expressing various combinations of the polymorphic forms of LIGHT (32S-214E/32S-214K, 32S-214E/32L-214E, and 32L-214E/32S-214K) were examined for binding avidity to LTβR-Fc, HVEM-Fc and DcR3-Fc using flow cytometry as in (A).
Figure 10:
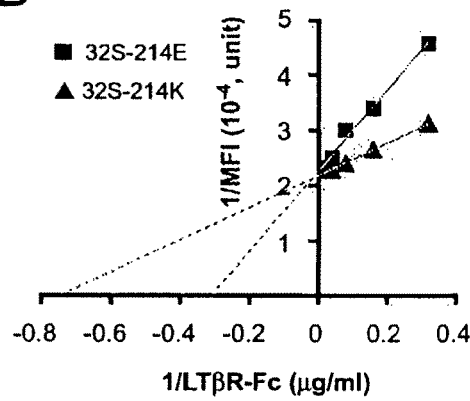
Figure 10:
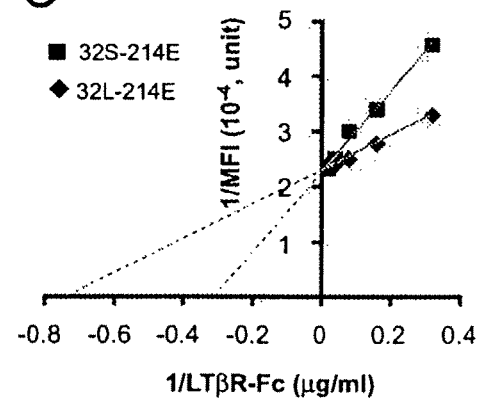
Figure 10:
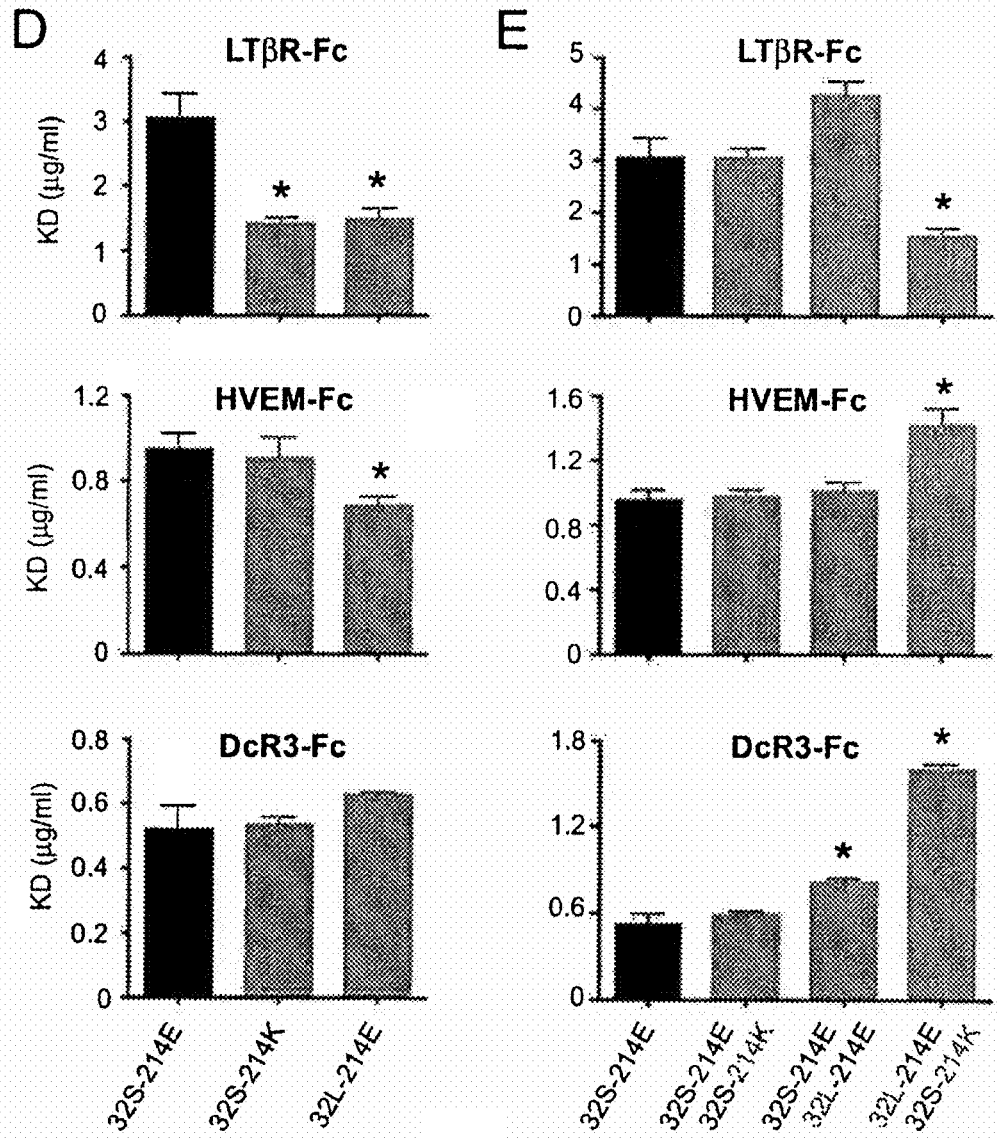
Figure 11:
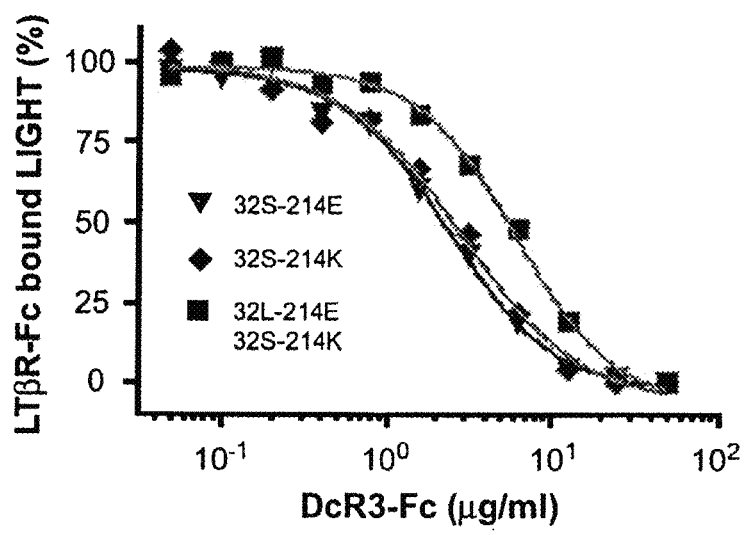
FIGS. 11A-11B. Competition binding assay for LTβR-Fc to LIGHT expressing EL4 cells in the presence of DcR3. (A) Graded concentrations of DcR3-Fc were incubated with various polymorphic forms of LIGHT (32S-214E, 32S-214K, 32L-214E/32S-214K) expressing EL4 cells in the presence of a constant concentration of LTβR-Fc. Specific LTβR-Fc binding to the LIGHT expressing EL4 cells was detected with an anti-LTβR monoclonal antibody (BD-A8). (B) IC50 values were calculated by nonlinear regression analysis using Prism GraphPad (v4; San Diego, USA).
Figure 11:
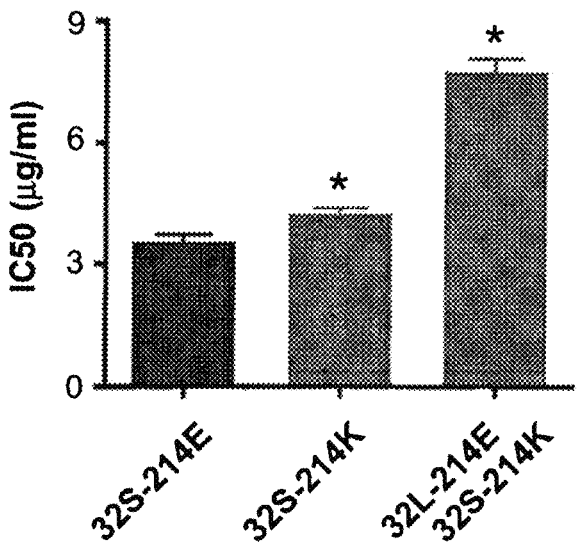

The efficacy of LIGHT in cancer-immunotherapy in humans is potentially adversely affected by DcR3 expressed by tumors in humans. Certain combinations of the variant forms of human LIGHT alter its binding affinity to human LTβR and human DcR3. A combination of LIGHT subunits (32L-214E and 32S-214K) enables LIGHT to attain a high affinity binding to human LTβR, but a reduced affinity for human DcR3 relative to the predominant form of human LIGHT (FIG. 10). Furthermore, the interaction between this heterotrimeric form of LIGHT 32L-214E/32S-214K and LTβR in the presence of DcR3 was evaluated.

Competition binding assays demonstrated that the inhibition concentration at 50% binding (IC50) of DcR3-Fc to the binding of LTβR to a combination of LIGHT-E214K (mutation from E to K at amino acid position 214) and LIGHT-S32L (mutation from S to L at amino acid position 32) is approximately 2.5 times higher than the predominant form of LIGHT (LIGHT 32S and 214E, FIG. 11, SEQ ID NO:1). In particular, 2.5 times higher concentration of DcR3-Fc was needed to inhibit binding of LTβR-Fc to the combination of LIGHT-E214K and LIGHT-S32L compared to the predominant form of LIGHT (SEQ ID NO:1). Thus, LIGHT-E214K and LIGHT-S32L could be a potent reagent for activating LTβR signaling system.

LIGHT variant 32L-214E/32S-214K molecule is therefore likely to be a more effective form for enhancing immune responses, particularly but not limited to cancer cells. Enhanced efficacy is due to high binding avidity to LTβR and low binding avidity to DcR3. As DcR3 has been found to be highly expressed in a wide variety of cancer cells, LIGHT variant 32L-214E/32S-214K will minimize the inhibitory effect of DcR3 towards the interaction between LIGHT and its receptors HVEM and LTβR. In addition, the high binding avidity of LIGHT 32L-214E/32S-214K to LTβR can also enhance anti-tumor activity mediated by LIGHT as the data above demonstrate that LTβR contributes to LIGHT-mediated anti-tumor responses.

What is claimed:

1. A method of promoting, stimulating, inducing or increasing T cell immunity against a hyperproliferative cell, tumor cell, cancer cell or metastatic cell comprising administering to a subject an amount of a cell having LTbeta receptor agonist attached, conjugated or coupled to the cell membrane effective to promote, stimulate, induce or increase the subject's T cell immunity against the hyperproliferative cell, tumor cell, cancer cell or metastatic cell wherein the LTbeta receptor agonist comprises the amino acid sequence selected from any one of SEQ ID NOs:4 to 10.

2. The method of claim 1, wherein the LTbeta receptor agonist comprises a LIGHT (p30 polypeptide) amino acid sequence with greater affinity for LTbR or HVEM as compared to native wild type LIGHT (p30 polypeptide).

3. The method of claim 1, wherein the LTbeta receptor agonist comprises SEQ ID NO:4.

4. The method of claim 1, wherein the LTbeta receptor agonist comprises SEQ ID NO:5.

5. The method of claim 1, wherein the LTbeta receptor agonist comprises SEQ ID NO:6.

6. The method of claim 1, wherein the LTbeta receptor agonist comprises SEQ ID NO:7.

7. The method of claim 1, wherein the LTbeta receptor agonist comprises SEQ ID NO:8.

8. The method of claim 1, wherein the LTbeta receptor agonist comprises SEQ ID NO:9.

9. The method of claim 1, wherein the LTbeta receptor agonist comprises SEQ ID NO:10.

* * * * *

SEQUENCE LISTING

<160> NUMBER OF SEQ ID NOS: 10

<210> SEQ ID NO 1
<211> LENGTH: 240
<212> TYPE: PRT
<213> ORGANISM: Homo sapiens

<400> SEQUENCE: 1

Met Glu Glu Ser Val Val Arg Pro Ser Val Phe Val Val Asp Gly Gln
1 5 10 15

Thr Asp Ile Pro Phe Thr Arg Leu Gly Arg Ser His Arg Arg Gln Ser
20 25 30

Cys Ser Val Ala Arg Val Gly Leu Gly Leu Leu Leu Leu Leu Met Gly
35 40 45

Ala Gly Leu Ala Val Gln Gly Trp Phe Leu Leu Gln Leu His Trp Arg
50 55 60

Leu Gly Glu Met Val Thr Arg Leu Pro Asp Gly Pro Ala Gly Ser Trp
65 70 75 80

Glu Gln Leu Ile Gln Glu Arg Arg Ser His Glu Val Asn Pro Ala Ala
85 90 95

His Leu Thr Gly Ala Asn Ser Ser Leu Thr Gly Ser Gly Gly Pro Leu
100 105 110

Leu Trp Glu Thr Gln Leu Gly Leu Ala Phe Leu Arg Gly Leu Ser Tyr
115 120 125

His Asp Gly Ala Leu Val Val Thr Lys Ala Gly Tyr Tyr Tyr Ile Tyr
130 135 140

Ser Lys Val Gln Leu Gly Gly Val Gly Cys Pro Leu Gly Leu Ala Ser
145 150 155 160

Thr Ile Thr His Gly Leu Tyr Lys Arg Thr Pro Arg Tyr Pro Glu Glu
165 170 175

Leu Glu Leu Leu Val Ser Gln Gln Ser Pro Cys Gly Arg Ala Thr Ser
180 185 190

Ser Ser Arg Val Trp Trp Asp Ser Ser Phe Leu Gly Gly Val Val His
195 200 205

Leu Glu Ala Gly Glu Glu Val Val Val Arg Val Leu Asp Glu Arg Leu
210 215 220

Val Arg Leu Arg Asp Gly Thr Arg Ser Tyr Phe Gly Ala Phe Met Val
225 230 235 240

```
<210> SEQ ID NO 2
<211> LENGTH: 175
<212> TYPE: PRT
<213> ORGANISM: Homo sapiens

<400> SEQUENCE: 2

Gly Glu Met Val Thr Arg Leu Pro Asp Gly Pro Ala Gly Ser Trp Glu
1               5                   10                  15

Gln Leu Ile Gln Glu Arg Arg Ser His Glu Val Asn Pro Ala Ala His
            20                  25                  30

Leu Thr Gly Ala Asn Ser Ser Leu Thr Gly Ser Gly Gly Pro Leu Leu
        35                  40                  45

Trp Glu Thr Gln Leu Gly Leu Ala Phe Leu Arg Gly Leu Ser Tyr His
    50                  55                  60

Asp Gly Ala Leu Val Val Thr Lys Ala Gly Tyr Tyr Tyr Ile Tyr Ser
65                  70                  75                  80

Lys Val Gln Leu Gly Gly Val Gly Cys Pro Leu Gly Leu Ala Ser Thr
                85                  90                  95

Ile Thr His Gly Leu Tyr Lys Arg Thr Pro Arg Tyr Pro Glu Glu Leu
            100                 105                 110

Glu Leu Leu Val Ser Gln Gln Ser Pro Cys Gly Arg Ala Thr Ser Ser
        115                 120                 125

Ser Arg Val Trp Trp Asp Ser Ser Phe Leu Gly Gly Val Val His Leu
    130                 135                 140

Glu Ala Gly Glu Glu Val Val Val Arg Val Leu Asp Glu Arg Leu Val
145                 150                 155                 160

Arg Leu Arg Asp Gly Thr Arg Ser Tyr Phe Gly Ala Phe Met Val
                165                 170                 175

<210> SEQ ID NO 3
<211> LENGTH: 240
<212> TYPE: PRT
<213> ORGANISM: Homo sapiens

<400> SEQUENCE: 3

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160
```

```
Thr Ile Thr His Gly Leu Tyr Lys Arg Thr Pro Arg Tyr Pro Glu Glu
            165                 170                 175

Leu Glu Leu Leu Val Ser Gln Gln Ser Pro Cys Gly Arg Ala Thr Ser
        180                 185                 190

Ser Ser Arg Val Trp Trp Asp Ser Ser Phe Leu Gly Gly Val Val His
        195                 200                 205

Leu Glu Ala Gly Glu Lys Val Val Arg Val Leu Asp Glu Arg Leu
        210                 215                 220

Val Arg Leu Arg Asp Gly Thr Arg Ser Tyr Phe Gly Ala Phe Met Val
225                 230                 235                 240
```

<210> SEQ ID NO 4
<211> LENGTH: 240
<212> TYPE: PRT
<213> ORGANISM: Homo sapiens

<400> SEQUENCE: 4

```
Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Leu
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240
```

<210> SEQ ID NO 5
<211> LENGTH: 240
<212> TYPE: PRT
<213> ORGANISM: Homo sapiens

<400> SEQUENCE: 5

```
Met Glu Glu Ser Val Val Arg Pro Ala Val Phe Val Val Asp Gly Gln
1               5                   10                  15
```

```
Thr Asp Ile Pro Phe Thr Arg Leu Gly Arg Ser His Arg Gln Ser
            20                  25                  30

Cys Ser Val Ala Arg Val Gly Leu Gly Leu Leu Leu Leu Met Gly
        35                  40                  45

Ala Gly Leu Ala Val Gln Gly Trp Phe Leu Leu Gln Leu His Trp Arg
 50                  55                  60

Leu Gly Glu Met Val Thr Arg Leu Pro Asp Gly Pro Ala Gly Ser Trp
 65                  70                  75                  80

Glu Gln Leu Ile Gln Glu Arg Arg Ser His Glu Val Asn Pro Ala Ala
                    85                  90                  95

His Leu Thr Gly Ala Asn Ser Ser Leu Thr Gly Ser Gly Gly Pro Leu
                100                 105                 110

Leu Trp Glu Thr Gln Leu Gly Leu Ala Phe Leu Arg Gly Leu Ser Tyr
            115                 120                 125

His Asp Gly Ala Leu Val Val Thr Lys Ala Gly Tyr Tyr Tyr Ile Tyr
130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
            195                 200                 205

Leu Glu Ala Gly Glu Glu Val Val Val Arg Val Leu Asp Glu Arg Leu
210                 215                 220

Val Arg Leu Arg Asp Gly Thr Arg Ser Tyr Phe Gly Ala Phe Met Val
225                 230                 235                 240

<210> SEQ ID NO 6
<211> LENGTH: 240
<212> TYPE: PRT
<213> ORGANISM: Homo sapiens

<400> SEQUENCE: 6

Met Glu Glu Ser Val Val Arg Pro Ser Val Phe Val Val Asp Gly Gln
 1               5                   10                  15

Thr Asp Ile Pro Phe Thr Arg Leu Gly Arg Ala His Arg Gln Ser
            20                  25                  30

Cys Ser Val Ala Arg Val Gly Leu Gly Leu Leu Leu Leu Met Gly
        35                  40                  45

Ala Gly Leu Ala Val Gln Gly Trp Phe Leu Leu Gln Leu His Trp Arg
 50                  55                  60

Leu Gly Glu Met Val Thr Arg Leu Pro Asp Gly Pro Ala Gly Ser Trp
 65                  70                  75                  80

Glu Gln Leu Ile Gln Glu Arg Arg Ser His Glu Val Asn Pro Ala Ala
                    85                  90                  95

His Leu Thr Gly Ala Asn Ser Ser Leu Thr Gly Ser Gly Gly Pro Leu
                100                 105                 110

Leu Trp Glu Thr Gln Leu Gly Leu Ala Phe Leu Arg Gly Leu Ser Tyr
            115                 120                 125

His Asp Gly Ala Leu Val Val Thr Lys Ala Gly Tyr Tyr Tyr Ile Tyr
130                 135                 140

Ser Lys Val Gln Leu Gly Gly Val Gly Cys Pro Leu Gly Leu Ala Ser
145                 150                 155                 160
```

```
Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Glu Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240
```

<210> SEQ ID NO 7
<211> LENGTH: 240
<212> TYPE: PRT
<213> ORGANISM: Homo sapiens

<400> SEQUENCE: 7

```
Met Glu Glu Ser Val Val Arg Pro Ala Val Phe Val Val Asp Gly Gln
1               5                   10                  15

Thr Asp Ile Pro Phe Thr Arg Leu Gly Arg Ala His Arg Arg Gln Ser
            20                  25                  30

Cys Ser Val Ala Arg Val Gly Leu Gly Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Glu Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240
```

<210> SEQ ID NO 8
<211> LENGTH: 240
<212> TYPE: PRT
<213> ORGANISM: Homo sapiens

<400> SEQUENCE: 8

```
Met Glu Glu Ser Val Val Arg Pro Ala Val Phe Val Val Asp Gly Gln
1               5                   10                  15
```

```
Thr Asp Ile Pro Phe Thr Arg Leu Gly Arg Ser His Arg Arg Gln Leu
             20                  25                  30

Cys Ser Val Ala Arg Val Gly Leu Gly Leu Leu Leu Leu Leu Met Gly
         35                  40                  45

Ala Gly Leu Ala Val Gln Gly Trp Phe Leu Leu Gln Leu His Trp Arg
 50                  55                  60

Leu Gly Glu Met Val Thr Arg Leu Pro Asp Gly Pro Ala Gly Ser Trp
 65                  70                  75                  80

Glu Gln Leu Ile Gln Glu Arg Arg Ser His Glu Val Asn Pro Ala Ala
                 85                  90                  95

His Leu Thr Gly Ala Asn Ser Ser Leu Thr Gly Ser Gly Gly Pro Leu
             100                 105                 110

Leu Trp Glu Thr Gln Leu Gly Leu Ala Phe Leu Arg Gly Leu Ser Tyr
         115                 120                 125

His Asp Gly Ala Leu Val Val Thr Lys Ala Gly Tyr Tyr Tyr Ile Tyr
 130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Glu Val Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240

<210> SEQ ID NO 9
<211> LENGTH: 240
<212> TYPE: PRT
<213> ORGANISM: Homo sapiens

<400> SEQUENCE: 9

Met Glu Glu Ser Val Val Arg Pro Ser Val Phe Val Val Asp Gly Gln
1                5                  10                  15

Thr Asp Ile Pro Phe Thr Arg Leu Gly Arg Ala His Arg Arg Gln Leu
             20                  25                  30

Cys Ser Val Ala Arg Val Gly Leu Gly Leu Leu Leu Leu Leu Met Gly
         35                  40                  45

Ala Gly Leu Ala Val Gln Gly Trp Phe Leu Leu Gln Leu His Trp Arg
 50                  55                  60

Leu Gly Glu Met Val Thr Arg Leu Pro Asp Gly Pro Ala Gly Ser Trp
 65                  70                  75                  80

Glu Gln Leu Ile Gln Glu Arg Arg Ser His Glu Val Asn Pro Ala Ala
                 85                  90                  95

His Leu Thr Gly Ala Asn Ser Ser Leu Thr Gly Ser Gly Gly Pro Leu
             100                 105                 110

Leu Trp Glu Thr Gln Leu Gly Leu Ala Phe Leu Arg Gly Leu Ser Tyr
         115                 120                 125

His Asp Gly Ala Leu Val Val Thr Lys Ala Gly Tyr Tyr Tyr Ile Tyr
 130                 135                 140

Ser Lys Val Gln Leu Gly Gly Val Gly Cys Pro Leu Gly Leu Ala Ser
```

```
145             150             155             160
Thr Ile Thr His Gly Leu Tyr Lys Arg Thr Pro Arg Tyr Pro Glu Glu
                165             170             175

Leu Glu Leu Leu Val Ser Gln Gln Ser Pro Cys Gly Arg Ala Thr Ser
            180              185             190

Ser Ser Arg Val Trp Trp Asp Ser Ser Phe Leu Gly Val Val His
        195             200             205

Leu Glu Ala Gly Glu Val Val Arg Val Leu Asp Glu Arg Leu
        210             215             220

Val Arg Leu Arg Asp Gly Thr Arg Ser Tyr Phe Gly Ala Phe Met Val
225             230             235             240

<210> SEQ ID NO 10
<211> LENGTH: 240
<212> TYPE: PRT
<213> ORGANISM: Homo sapiens

<400> SEQUENCE: 10

Met Glu Glu Ser Val Val Arg Pro Ala Val Phe Val Val Asp Gly Gln
1               5               10              15

Thr Asp Ile Pro Phe Thr Arg Leu Gly Arg Ala His Arg Arg Gln Leu
                20              25              30

Cys Ser Val Ala Arg Val Gly Leu Gly Leu Leu Leu Leu Leu Met Gly
            35              40              45

Ala Gly Leu Ala Val Gln Gly Trp Phe Leu Leu Gln Leu His Trp Arg
        50              55              60

Leu Gly Glu Met Val Thr Arg Leu Pro Asp Gly Pro Ala Gly Ser Trp
65              70              75              80

Glu Gln Leu Ile Gln Glu Arg Arg Ser His Glu Val Asn Pro Ala Ala
                85              90              95

His Leu Thr Gly Ala Asn Ser Ser Leu Thr Gly Ser Gly Gly Pro Leu
            100             105             110

Leu Trp Glu Thr Gln Leu Gly Leu Ala Phe Leu Arg Gly Leu Ser Tyr
        115             120             125

His Asp Gly Ala Leu Val Val Thr Lys Ala Gly Tyr Tyr Tyr Ile Tyr
    130             135             140

Ser Lys Val Gln Leu Gly Gly Val Gly Cys Pro Leu Gly Leu Ala Ser
145             150             155             160

Thr Ile Thr His Gly Leu Tyr Lys Arg Thr Pro Arg Tyr Pro Glu Glu
                165             170             175

Leu Glu Leu Leu Val Ser Gln Gln Ser Pro Cys Gly Arg Ala Thr Ser
            180             185             190

Ser Ser Arg Val Trp Trp Asp Ser Ser Phe Leu Gly Val Val His
        195             200             205

Leu Glu Ala Gly Glu Val Val Arg Val Leu Asp Glu Arg Leu
        210             215             220

Val Arg Leu Arg Asp Gly Thr Arg Ser Tyr Phe Gly Ala Phe Met Val
225             230             235             240
```